United States Patent [19]

Warrellow et al.

[11] Patent Number: 5,739,144

[45] Date of Patent: Apr. 14, 1998

[54] TRISUBSTITUTED PHENYL DERIVATIVES

[75] Inventors: Graham John Warrellow, Northwood; Valerie Anne Cole, Burnham; Rikki Peter Alexander, High Wycombe, all of United Kingdom

[73] Assignee: Celltech Therapeutics Limited, Slough, United Kingdom

[21] Appl. No.: 543,962

[22] Filed: Oct. 17, 1995

Related U.S. Application Data

[63] Continuation of Ser. No. 384,612, Feb. 2, 1995, abandoned, which is a continuation of Ser. No. 208,656, Mar. 9, 1994, abandoned.

[30] Foreign Application Priority Data

Mar. 10, 1993 [GB] United Kingdom ............... 9304920

[51] Int. Cl.$^6$ ................... A61K 31/44; C07D 213/16
[52] U.S. Cl. ................... 514/277; 514/357; 546/329; 546/339
[58] Field of Search ................... 546/329, 339; 514/222, 357

[56] References Cited

U.S. PATENT DOCUMENTS

| | | | |
|---|---|---|---|
| 4,012,495 | 3/1977 | Schmiechen et al. | 424/274 |
| 4,015,017 | 3/1977 | Gazave | 424/331 |
| 4,153,713 | 5/1979 | Huth et al. | 424/274 |
| 4,193,926 | 3/1980 | Schmiechen et al. | 260/326.5 |
| 4,303,649 | 12/1981 | Jones | 424/177 |
| 4,788,195 | 11/1988 | Torley et al. | 514/252 |
| 4,792,561 | 12/1988 | Walker et al. | 514/312 |
| 4,876,252 | 10/1989 | Torley et al. | 514/224.8 |
| 4,897,396 | 1/1990 | Hubele | 514/275 |
| 4,921,862 | 5/1990 | Walker et al. | 514/312 |
| 4,966,622 | 10/1990 | Rempfler et al. | 71/92 |
| 4,971,959 | 11/1990 | Hawkins | 514/150 |
| 5,124,455 | 6/1992 | Lombardo | 546/181 |
| 5,128,358 | 7/1992 | Saccomano et al. | 514/392 |
| 5,159,078 | 10/1992 | Rempfler et al. | 544/330 |
| 5,175,167 | 12/1992 | Zipperer et al. | 514/277 |
| 5,177,085 | 1/1993 | Naef | 514/307 |
| 5,236,918 | 8/1993 | Amschler et al. | 514/247 |
| 5,274,002 | 12/1993 | Hawkins | 514/530 |
| 5,298,511 | 3/1994 | Waterson | 514/311 |
| 5,326,898 | 7/1994 | Chandraratna | 560/17 |

(List continued on next page.)

FOREIGN PATENT DOCUMENTS

| | | |
|---|---|---|
| 0 233 461 A2 | 8/1987 | European Pat. Off. . |
| 0 295 210 A1 | 12/1988 | European Pat. Off. . |
| 0 337 943 A2 | 10/1989 | European Pat. Off. . |
| 0 393 500 | 10/1990 | European Pat. Off. . |
| 0 490 823 | 6/1991 | European Pat. Off. . |
| 0 470 805 | 2/1992 | European Pat. Off. . |
| 0497564A1 | 8/1992 | European Pat. Off. . |
| 0 511 865 | 11/1992 | European Pat. Off. . |
| 0 537 742 | 4/1993 | European Pat. Off. . |
| 0 564 409 A1 | 10/1993 | European Pat. Off. . |
| 2 545 356 A1 | 11/1984 | France . |
| 3-77872 | 4/1991 | Japan . |
| 3-77923 | 4/1991 | Japan . |
| 1588639 | 4/1981 | United Kingdom . |
| WO 87/06576 | 11/1987 | WIPO . |

(List continued on next page.)

OTHER PUBLICATIONS

Ashton, "Selective Type IV Phosphodiesterase Inhibitors as Antiasthmatic Agents. The Syntheses and Biological Activities of 3-(Cyclopentyloxy)-4-methyoxybenzamides and Analogues" J. Med. Chem. 37: 1696-1703 (1994).

Beavo & Reifsnyder, "Primary Sequence of Cyclic Nucleotide Phosphodiesterase Isozymes and the Design of Selective Inhibitors" TIPS 11: 150-155 (1990).

Buu-Hoi, N.P. et al., "Bromination of Some 1,2,2-Triarylethylenes" J. of Organic Chemistry, 1261-1263 (Sep., 1958).

Buu-Hoi et al., "New Method for the Synthesis of ω,ω-Diarylacetophenones Aminated in the Aromatic Nucleus. Plynitration of Triarylethylenes" Chemical Abstracts 61: 16006h (1964).

El-Wakil et al., "Study of the proton magnetic resonance of methoxytamoxifen towards ortho-substitution" Chemical Abstracts 116: 255248t (1992) Mar.

(List continued on next page.)

Primary Examiner—Gary Geist
Assistant Examiner—Rosalynd Keys
Attorney, Agent, or Firm—Woodcock Washburn Kurtz Mackiewicz & Norris LLP

[57] ABSTRACT

Compounds of general formula (1)

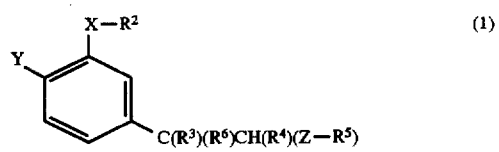

are described wherein Y is a halogen atom or a group —OR$^1$, where R$^1$ is an optionally substituted alkyl group; X is —O—, —S— or —N(R$^7$)—, where R$^7$ is a hydrogen atom or an alkyl group; R$^2$ is an optionally substituted cycloalkyl or cycloalkenyl group; R$^3$ and R$^4$, which may be the same or different, is each a hydrogen atom or an alkyl, —CO$_2$R$^8$ (where R$^8$ is a hydrogen atom or an alkyl, aryl, or aralkyl group), —CONR$^9$R$^{10}$ (where R$^9$ and R$^{10}$ which may be the same or different is each a hydrogen atom or an alkyl, aryl or aralkyl group), —CSNR$^9$R$^{10}$, —CN, —CH$_2$CN group; Z is —(CH$_2$)$_n$— (where n is zero or an integer 1, 2 or 3; R$^5$ is an optionally substituted monocyclic or bicyclic aryl group optionally containing one or more heteroatoms selected from oxygen, sulphur or nitrogen atoms; R$^6$ is a hydrogen atom or a hydroxyl group; and the salts, solvates, hydrates, prodrugs and N-oxides thereof. Compounds according to the invention are potent and selective phosphodiesterase type IV inhibitors and are useful in the prophylaxis and treatment of diseases such as asthma where an unwanted inflammatory response or muscular spasm is present.

17 Claims, No Drawings

U.S. PATENT DOCUMENTS

| | | | |
|---|---|---|---|
| 5,340,827 | 8/1994 | Beeley et al. | 514/352 |
| 5,491,147 | 2/1996 | Boyd et al. | 514/247 |
| 5,550,137 | 8/1996 | Beeley et al. | 514/354 |
| 5,580,888 | 12/1996 | Warrellow et al. | 514/332 |
| 5,608,070 | 3/1997 | Alexander et al. | 546/270 |

FOREIGN PATENT DOCUMENTS

| | | |
|---|---|---|
| WO 91/15451 | 10/1991 | WIPO . |
| WO 91/16892 | 11/1991 | WIPO . |
| WO 92/00968 | 1/1992 | WIPO . |
| WO 92/06085 | 4/1992 | WIPO . |
| WO 92/06963 | 4/1992 | WIPO . |
| WO 92/07567 | 5/1992 | WIPO . |
| WO 92/12961 | 8/1992 | WIPO . |
| WO 92/19594 | 11/1992 | WIPO . |
| WO 92/19602 | 11/1992 | WIPO . |
| WO 93/19748 | 10/1993 | WIPO . |
| WO 94/02465 | 2/1994 | WIPO . |
| WO 94/12461 | 6/1994 | WIPO . |
| WO 94/20455 | 9/1994 | WIPO . |
| WO 95/09847 | 4/1995 | WIPO . |
| WO 95/09851 | 4/1995 | WIPO . |
| WO 95/09852 | 4/1995 | WIPO . |
| WO 95/09853 | 4/1995 | WIPO . |
| WO 95/17386 | 6/1995 | WIPO . |

OTHER PUBLICATIONS

Hirose et al., "Styrene Derivatives and Electrophotpgraphic Photoreceptor Containing Them" Chemical Abstracts 118: 136183z (1993).

Lisle, H. et al., "IL–2–Induced Eosinophilia in the Rat Pleural Cavity: The Effect of Dexamethasone and Indomethacin", Br. J. Pharmacol. 1993, 108, 230.

Livi et al., "Cloning and Expression of cDNA for a Human Low–$K_m$3 Rolipram–sensitive Cyclic AMP Phosphodiesterase", Molecular and Cellular Biol. 1990, 10, 2678.

Ishikura, M. et al., "An Efficient Synthesis of 3–Heteroarylpyridines via Diethyl–(3–pyridyl)–borane" Synthesis pp. 936–938 (1984).

Manhas et al., "heterocyclic Compounds XII. Quinazoline Derivatives as Potential Antifertility Agents(1)" J. Heterocyclic Chem: 711–715 (1979) Jun.

Meyers, A.J. et al., "Oxazolines. XI. Synthesis of Functionalized Aromatic and Aliphatic Acids. A Useful Protecting Group for Carboxylic Acids Against Grignard and Hydride Reagents", J. Org. Chem. 1974, 39, 2787.

Mezheritskaya, "Synthesis and properties of carboxonium het=erocyclic systems. VII. Synthesis and properties of 2–benzyl–substituted 1,3–dioxolanium salts" Chem. Abs. 93: 95160j p. 635 (1980) Jan.

Mitsunobu, O., "The Use of Diethyl Azodicarboxylate and Triphenylphosphine in Synthesis and Transformation of Natural Products" Synthesis 1–28 (1981).

Nicholson et al., "Differential Modulation of Tissue Function and Therapeutic Potential of Selective Inhibitors of Cyclic Nucleotide Phosphodiesterase Isoenzymes" TIPS 12: 19–27 (1991).

O'Connor et al., "Voltammetry and Controlled Potential Oxidation of 3,4–dimethoxypropenylbenzene at a rotating platinum electrode in unbuffered acetonitrile and in acetonitrile–pyridine solution" Chemical Abstracts 60(8) #10203.4 (Apr. 13, 1964).

Porter et al., "Preparation of 6–phneyl–3–(5–tetrazolyl)pyridin=2(H)–one Derivatives as Cyclic AMP–dependent Protein Kinase Agonists" Chem. Abstract 117(9): 90296n (1992).

Ramalingam, Deshmukh and Sattur, "Synthesis and Pharmacology of 2,5–Disubstituted 1,3,4–Zxadiazoles" J. Indian Chem. Soc. vol. 58(3) 269–271 (1981) Mar.

Reddy et al., "Inhibition of Breast Cancer Cell Growth in Vitro by a Tyrosine Kinase Inhibitor" Cancer Research 52: 3636–3641 (1992) Jul.

Schneider et al., "Catechol Estrogens of the 1,1, 2–Triphenylbut–1–ene Type: Relationship Between Structure, Estradiol Receptor Affinity, Estrogenic and Antiestrogenic Properties, and Mammary Tumor Inhibiting Activities" J. Med. Chem. 29: 1355–1362 (1986).

Seitz et al., "Fluorotamoxifen. A Caveat on the Generality of Electrophilic Destannylation" Chemical Abstracts 111: 57136k (1989).

Sharp, M.J. et al., "Synthetic Connections to the Aromatic Directed Metalation Reaction. Functionalized Aryl Boronic Acids by Ipso Borodesilylation; General Synthesis of Unsymmetrical iphenyls and n–Terphenyls" Tetrahedron Lett 28: 5093–5096 (1987).

Thompson, W.J. and Gaudino, J., "A General Synthesis of 5–Arylnicotinates" J. Org. Chem. 49: 5237–5243 (1984).

Yeadon et al., "Mechanisms Contributing to Ozone–Induced Bronchial Hyperreactivity in Guinea Pigs", Pulmonary Pharm. 1992, 5, 39.

Yoneda et al., "The Antiproliferative Effects of Tyrosine Kinase Inhibitors Tyrphostins on a Human Squamous Cell Carcinoma in Vitro and in Nude Mice" Cancer Research 51: 4430–4435 (1991).

Chan, A.C. et al., "The Role of Protein Tyrosine Kinases and Protein Tyrosine Phosphatases in T Cell Antigen Receptor Signal Transduction", Annu. Rev. Immunol., 1994, 12, 555–592.

Daves, G.D. et al., "Pyrimidines. XIII. 2–and 6–Substituted 4–Pyrimidinecarboxylic Acids", J. of Hev. Chem., 1964, 1, 130–133 Jul.

Dietl, F. et al., "Chinone von Benzo–und Dibenzokronenethern", Synthesis, 1985, 626–631.

Geissler, J.F. et al., "Thiazolidine–Diones. Biochemical and Biological Activity of a Novel Class of Tyrosine Protein Kinase Inhibitors", J. of Biol. Chem., 1990, 265(36), 22255–22261 Jul.

Hanks, S.K. et al., "The eukaryotic protein kinase superfamily: kinase (catalytic) domain structure and classification", FASEB J., 1995, 9, 576–596.

Iwashita, S. et al., "Signal Transduction System for Growth Factor Receptors Associated with Tyrosine Kinase Activity: Epidermal Growth Factor Receptor Singalling and Its Regulation", Cellular Signalling, 1992, 4(2), 123–132.

Newton, A.C., "Protein Kinase C: Structure, Function, Regulation", J. Biol. Chem., 1995, 270(48), 28495–28498.

Ohtani, Y. et al., "Studies on Pitch Problems Caused by Pulping and Bleaching of Tropical Woods. XIV. Chemistry of the Aurone Derivatives at the Conventional Bleaching Stages", Acta Chem. Scand., 1982, 613–621.

Pines, J., "Cyclins and cyclin–dependent kinases: take your partners", *TIBS*, 1993, 18, 195–197 Jun.

Plé, N. et al., "Metalation of Diazines. XI. Directed Ortho–Lithiation of Fluoropyrimidines and Application to Synthesis of an Azacarboline", *J. Heterocyclic Chem.*, 1994, 31, 1311–1315 Nov.–Dec.

Sánchez, H.I. et al., "Formal Total Synthesis of β–Pipitzol", *Tetrahedron*, 1985, 41(12), 2355–2359.

Sakakibara, K. et al., "Preparation of N-pyridyl-4-(benzyloxy)benzamides as Cardiotonics", *Chem. Abstr.* 1988, 108, No. 131583p.

Tsutsumi, K. et al., "Preparation of (Dialkoxyphosphinoylmethyl)benzamides as Antihyperlipidemics", *Chem. Abstr.* 1990, 113, No. 6599a.

TRISUBSTITUTED PHENYL DERIVATIVES

This is a continuation of U.S. application Ser. No. 08/384,612, filed Feb. 2, 1995 abandoned, which is a continuation of U.S. application Ser. No. 08/208,656, filed Mar. 9, 1994 abandoned.

This invention relates to a novel series of tri-substituted phenyl derivatives, to processes for their preparation, to pharmaceutical compositions containing them, and to their use in medicine.

Many hormones and neurotransmitters modulate tissue function by elevating intra-cellular levels of adenosine 3',5'-cyclic monophosphate (cAMP). The cellular levels of cAMP are regulated by mechanisms which control synthesis and breakdown. The synthesis of cAMP is controlled by adenylyl cyclase which may be directly activated by agents such as forskolin or indirectly activated by the binding of specific agonists to cell surface receptors which are coupled to adenylyl cyclase. The breakdown of cAMP is controlled by a family of phosphodiesterase (PDE) isoenzymes, which also control the breakdown of guanosine 3',5'-cyclic monophosphate (cGMP). To date, seven members of the family have been described (PDE I–VII) the distribution of which varies from tissue to tissue. This suggests that specific inhibitors of PDE isoenzymes could achieve differential elevation of cAMP in different tissues. [for reviews of PDE distribution, structure, function and regulation, see Beavo & Reifsnyder (1990) TIPS, 11.: 150–155 and Nicholson et al (1991) TIPS, 12: 19–27.

There is clear evidence that elevation of cAMP in inflammatory leukocytes leads to inhibition of their activation. Furthermore, elevation of cAMP in airway smooth muscle has a spasmolytic effect. In these tissues, PDE IV plays a major role in the hydrolysis of cAMP. It can be expected, therefore, that selective inhibitors of PDE IV would have therapeutic effects in inflammatory diseases such as asthma, by achieving both anti-inflammatory and bronchodilator effects.

The design of PDE IV inhibitors has met with limited success to date, in that many of the potential PDE IV inhibitors which have been synthesised have lacked potency and/or have been capable of inhibiting more than one type of PDE isoenzyme in a non-selective manner. Lack of a selective action has been a particular problem given the widespread role of cAMP in vivo and what is needed are potent selective PDE IV inhibitors with an inhibitory action against PDE IV and little or no action against other PDE isoenzymes.

We have now found a novel series of tri-substituted phenyl derivatives, members of which, compared to known structurally similar compounds, are potent inhibitors of PDE IV at concentrations at which they have little or no inhibitory action on other PDE isoenzymes. These compounds inhibit the isolated PDE IV enzyme and also elevate cAMP in isolated leukocytes. Certain compounds prevent inflammation in the lungs or pleural cavity induced by carrageenan, platelet-activating factor (PAF), interleukin-5 (IL-5) or antigen challenge. These compounds also suppress the hyper-responsiveness of airway smooth muscle seen in inflamed lungs. Advantageously, compounds according to the invention have good oral activity and at orally effective doses exhibit little or none of the side-effects associated with known PDE IV inhibitors, such as rolipram. The compounds of the invention are therefore of use in medicine, especially in the prophylaxis and treatment of asthma.

Thus according to one aspect of the invention, we provide a compound of formula (1)

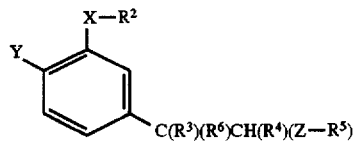

wherein

Y is a halogen atom or a group —OR$^1$, where R$^1$ is an optionally substituted alkyl group;

X is —O—, —S—, or —N(R$^7$)—, where R$^7$ is a hydrogen atom or an alkyl group;

R$^2$ is an optionally substituted cycloalkyl or cycloalkenyl group;

R$^3$ and R$^4$, which may be the same or different, is each a hydrogen atom or an optionally substituted alkyl, —CO$_2$R$^8$ (where R$^8$ is a hydrogen atom or an optionally substituted alkyl, aryl or aralkyl group), —CONR$^9$R$^{10}$ (where R$^9$ and R$^{10}$ which may be the same or different is as described for R$^8$), —CSNR$^9$R$^{10}$, —CN, or —CH$_2$CN group;

Z is —(CH$_2$)$_n$— where n is zero or an integer 1, 2 or 3;

R$^5$ is an optionally substituted monocyclic or bicyclic aryl group optionally containing one or more heteroatoms selected from oxygen, sulphur or nitrogen atoms;

R$^6$ is a hydrogen atom or a hydroxyl group; and the salts, solvates, hydrates, prodrugs and N-oxides thereof.

It will be appreciated that the compounds of formula (1) may have one or more chiral centres, depending on the nature of the groups R$^3$, R$^4$, R$^5$, R$^6$ and Z. Where one or more chiral centres is present, enantiomers or diastereomers may exist, and the invention is to be understood to extend to all such enantiomers, diastereomers and mixtures thereof, including racemates.

In the following description, a reference to an alkyl group, whether it is an individual group or part of a larger group, is intended to mean, where possible, a straight or branched alkyl group.

In the compounds of formula (1), when Y is a halogen atom it may be for example a fluorine, chlorine, bromine or iodine atom.

When Y in the compounds of formula (1) is a group —OR$^1$, R$^1$ may be, for example, an optionally substituted C$_{1-3}$alkyl group, such as a methyl, ethyl, n-propyl, or i-propyl group. Optional substitutents which may be present on R$^1$ groups include one or more halogen atoms, e.g. fluorine, or chlorine atoms.

When X in compounds of formula (1) is a —N(R$^7$)— group it may be a —NH— group or a group —N(R$^6$)— where R$^6$ is an optionally substituted C$_{1-6}$alkyl group such as a methyl or ethyl group.

When R$^2$ in the compounds of formula (1) is an optionally substituted cycloalkyl or cycloalkenyl group it may be for example a C$_{3-8}$cycloalkyl group such as a cyclobutyl, cyclopentyl or cyclohexyl group or a C$_{3-8}$cycloalkenyl group containing for example one or two double bonds such as a 2-cyclobuten-1-yl, 2-cyclopenten-1-yl, 3-cyclopenten-1-yl, 2,4-cyclopentadien-1-yl, 2-cyclohexen-1-yl, 3-cyclohexen-1-yl, 2,4-cyclohexadien-1-yl or 3,5-cyclohexadien-1-yl group, each cycloalkyl or cycloalkenyl group being optionally substituted by one, two or three substituents selected from halogen atoms, e.g. fluorine, chlorine, bromine or iodine atoms, straight or branched C$_{1-6}$alkyl e.g. C$_{1-3}$alkyl such as methyl or ethyl, hydroxyl or C$_{1-6}$alkoxy e.g. C$_{1-3}$alkoxy such as methoxy or ethoxy groups.

Alkyl groups represented by R$^3$ and R$^4$ in compounds of formula (1) include C$_{1-6}$alkyl groups, for example C$_{1-3}$alkyl groups, such as methyl, ethyl, n-propyl or i-propyl groups. Optional substituents which may be present on $R^3$ or $R^4$ include one or more halogen atoms, e.g. fluorine, chlorine, bromine or iodine atoms, or hydroxyl or $C_{1-6}$alkoxy e.g. $C_{1-3}$alkoxy such as methoxy or ethoxy groups, or thiol or $C_{1-6}$ alkylthio e.g. $C_{1-3}$alkylthio such as methylthio or ethylthio groups.

Particular examples of $R^3$ or $R^4$ alkyl groups include —$CH_3$, —$CH_2CH_3$, —$CH_2OH$, —$CH_2Cl$, —$CH_2F$, —$CHCl_2$, —$CHF_2$ and —$CH_2OCH_3$ groups.

When $R^3$ and/or $R^4$ is a —$CO_2R^8$, —$CONR^9R^{10}$ or $CSNR^9R^{10}$ group it may be for example a —$CO_2H$, —$CONH_2$, or —$CSNH_2$ group, or a group —$CO_2R^8$, —$CONR^9R^{10}$, —$CSNR^9R^{10}$ —$CONHR^{10}$ or —$CSNHR^{10}$ wherein $R^8$, $R^9$ and $R^{10}$ where present is a $C_{1-3}$alkyl group such as a methyl or ethyl group, a $C_{6-12}$aryl group, for example an optionally substituted phenyl, or a 1- or 2-naphthyl group, or a $C_{6-12}$aryl $C_{1-3}$alkyl group such as an optionally substituted benzyl or phenethyl group. Optional substituents which may be present on these groups include $R^{11}$ substituents discussed below in relation to the group $R^5$.

In the compounds of formula (1) Z may represent a bond connecting the group $R^5$ to the rest of the molecule, or represents a group —$CH_2$—, —$(CH_2)_2$— or $(CH_2)_3$—.

Monocyclic or bicyclic aryl groups represented by the group $R^5$ in compounds of formula (1) include for example $C_{6-12}$ optionally substituted aryl groups, for example optionally substituted phenyl, 1- or 2-naphthyl, indenyl or isoindenyl groups.

When the monocyclic or bicyclic aryl group contains one or more heteroatoms it may be a $C_{1-9}$, for example a $C_{3-9}$, optionally substituted heteroaryl group containing for example one, two, three or more heteroatoms selected from oxygen, sulphur or nitrogen atoms. In general, heteroaryl groups may be for example monocyclic or bicyclic heteroaryl groups. Monocyclic heteroaryl groups include for example five- or six-membered heteroaryl groups containing one, two, three or four heteroatoms selected from oxygen, sulphur or nitrogen atoms.

Examples of heteroaryl groups represented by Ar include pyrrolyl, furyl, thienyl, imidazolyl, N-methylimidazolyl, N-ethylimidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl, pyridyl, pyrimidinyl, pyridazinyl, pyrazinyl, 1,3,5-triazinyl, 1,2,4-triazinyl, 1,2,3-triazinyl, benzofuryl, isobenzofuryl, benzothienyl, isobenzothienyl, indolyl, isoindolyl, benzimidazolyl, benzothiazolyl, benzoxazolyl, quinazolinyl, naphthyridinyl, pyrido[3,4-b]pyridyl, pyrido[3,2-b]pyridyl, pyrido[4,3-b]pyridyl, quinolinyl, isoquinolinyl, tetrazolyl, 5,6,7,8-tetrahydroquinolinyl and 5,6,7,8-tetrahydroisoquinolinyl.

The heteroaryl group represented by $R^5$ may be attached to the remainder of the molecule of formula (1) through any ring carbon or heteroatom as appropriate. Thus, for example, when the group Ar is a pyridyl group it may be a 2-pyridyl, 3-pyridyl or 4-pyridyl group. When it is a thienyl group it may be a 2-thienyl or 3-thienyl group, and, similarly, when it is a furyl group it may be a 2-furyl or 3-furyl group.

When in compounds of formula (1) the heteroaryl group is a nitrogen-containing heterocycle it may be possible to form quaternary salts, for example N-alkyl quaternary salts and the invention is to be understood to extend to such salts. Thus for example when the group Ar is a pyridyl group, pyridinium salts may be formed, for example N-alkylpyridinium salts such as N-methylpyridinium.

The aryl or heteroaryl groups represented by $R^5$ in compounds of formula (1) may each optionally be substituted by one, two, three or more substituents [$R^{11}$]. The substituent $R^{11}$ may be selected from an atom or group $R^{12}$ or —$Alk^1$ ($R^{12})_m$ wherein $R^{12}$ is a halogen atom, or an amino (—NH2), substituted amino, nitro, cyano, hydroxyl (—OH), substituted hydroxyl, cycloalkoxy, formyl [HC(O)—], carboxyl (—$CO_2H$), esterified carboxyl, thiol (—SH), substituted thiol, —$C(O)R^{8a}$ [where $R^{8a}$ is as defined above for $R^8$], —$SO_3H$, —$SO_2R^{8a}$, —$SO_2N(R^{8a})(R^{9a})$, (where $R^{9a}$ is as described above for $R^{8a}$ and may be the same as or different to $R^{8a}$, —$CON(R^{8a})(R^{9a})$, —$NHSO_2R^{8a}$, —$N[SO_2R^{8a}]_2$, —$NHSO_2N(R^{8a})(R^{9a})$, —$NHC(O)R^{8a}$, or —$NHC(O)OR^{8a}$ group; $Alk^1$ is a straight or branched $C_{1-6}$alkylene, $C_{2-6}$alkenylene, or $C_2$-alkynylene chain optionally interrupted by one, two, or three —O—, or —S— atoms or —S(O)p—, [where p is an integer 1 or 2] or —$N(R^7)$— groups; and m is zero or an integer 1, 2 or 3.

When in the group —$Alk^1(R^{12})_m$ m is an integer 1, 2 or 3, it is to be understood that the substituent or substituents $R^{12}$ may be present on any suitable carbon atom in —$Alk^1$. Where more than one $R^{12}$ substitutent is present these may be the same or different and may be present on the same or different carbon atom in $Alk^1$. Clearly, when m is zero and no substituent $R^{12}$ is present the alkylene, alkenylene or alkynylene chain represented by $Alk^1$ becomes an alkyl, alkenyl or alkynyl group.

When $R^{12}$ is a substituted amino group it may be a group —$NH[Alk^1(R^{13})_m]$ [where $Alk^1$ and m are as defined above and $R^{13a}$ is as defined above for $R^{12}$ but is not a substituted amino, a substituted hydroxyl or a substituted thiol group] or a group —$N[Alk^1(R^{13})_m]_2$ wherein each —$Alk^1(R^{13})_m$ group is the same or different.

When $R^{12}$ is a halogen atom it may be for example a fluorine, chlorine, bromine, or iodine atom.

When $R^{12}$ is a cycloalkoxy group it may be for example a $C_{5-7}$cycloalkoxy group such as a cyclopentyloxy or cyclohexyloxy group.

When $R_{12}$ is a substituted hydroxyl or substituted thiol group it may be a group —$OAlk^1(R^{13})_m$ or —$SAlk^1(R^{13})_m$ respectively, where $Alk^1$, $R^{13}$ and m are as just defined.

Esterified carboxyl groups represented by the group $R^{12}$ include groups of formula —$CO_2Alk^2$ wherein $Alk^2$ is a straight or branched, optionally substituted $C_{1-8}$alkyl group such as a methyl, ethyl, n-propyl, i-propyl, n-butyl, i-butyl, s-butyl or t-butyl group; a $C_{6-12}$aryl$C_{1-8}$alkyl group such as an optionally substituted benzyl, phenylethyl, phenylpropyl, 1-naphthylmethyl or 2-naphthylmethyl group; a $C_{6-12}$aryl group such as an optionally substituted phenyl, 1-naphthyl or 2-naphthyl group; a $C_{6-12}$aryloxy$C_{1-8}$alkyl group such as an optionally substituted phenyloxymethyl, phenyloxyethyl, 1-naphthyloxymethyl, or 2-naphthyloxymethyl group; an optionally substituted $C_{1-8}$alkanoyloxy$C_{1-8}$alkyl group, such as a pivaloyloxymethyl, propionyloxyethyl or propionyloxypropyl group; or a $C_{6-12}$aroyloxy$C_{1-8}$alkyl group such as an optionally substituted benzoyloxyethyl or benzoyloxypropyl group. Optional substituents present on the $Alk^2$ group include $R^{11}$ substituents described above.

When $Alk^1$ is present in or as a substituent $R^{11}$ it may be for example a methylene, ethylene, n-propylene, i-propylene, n-butylene, i-butylene, s-butylene, t-butylene, ethenylene, 2-propenylene, 2-butenylene, 3-butenylene, ethynylene, 2-propynylene, 2-butynylene or 3-butynylene chain, optionally interrupted by one, two, or three —O— or —S—, atoms or —S(O)—, —$S(O)_2$— or —$N(R^7)$— groups.

Particularly useful atoms or groups represented by $R^{11}$ include fluorine, chlorine, bromine or iodine atoms, or $C_{1-6}$alkyl, e.g. methyl or ethyl, $C_{1-6}$alkylamino, e.g. methylamino or ethylamino, $C_{1-6}$hydroxyalkyl, e.g. hydroxymethyl or hydroxyethyl, $C_{1-6}$alkylthiol e.g. methylthiol or ethylthiol, $C_{1-6}$alkoxy, e.g. methoxy or ethoxy, $C_{5-7}$cycloalkoxy, e.g. cyclo-pentyloxy, halo$C_{1-6}$alkyl, e.g. trifluoromethyl, $C_{1-6}$alkylamino, e.g. methylamino or ethylamino, amino (—$NH_2$), amino$C_{1-6}$alkyl, e.g. aminomethyl or aminoethyl, $C_{1-6}$dialkylamino, e.g. dimethylamino or diethylamino, nitro, cyano, hydroxyl (—OH), formyl [HC(O)—], carboxyl (—$CO_2H$), —$CO_2Alk^2$ [where $Alk^2$ is as defined above], $C_{1-6}$ alkanoyl e.g. acetyl, thiol (—SH), thio$C_{1-6}$alkyl, e.g. thiomethyl or thioethyl, sulphonyl (—$SO_3H$), $C_{1-6}$alkylsulphonyl, e.g. methylsulphonyl, aminosulphonyl (—$SO_2NH_2$), $C_{1-6}$alkylaminosulphonyl, e.g. methylaminosulphonyl or ethylaminosulphonyl, $C_{1-6}$dialkylaminosulphonyl, e.g. dimethylaminosulphonyl or diethylaminosulphonyl, arylaminosulphonyl, e.g. optionally substituted phenylaminosulphonyl, aralkylaminosulphonyl, e.g. optionally substituted benzylaminosulphonyl, carboxamido (—$CONH_2$), $C_{1-6}$alkylaminocarbonyl, e.g. methylaminocarbonyl or ethylaminocarbonyl, $C_{1-6}$dialkylaminocarbonyl, e.g. dimethylaminocarbonyl or diethylaminocarbonyl, sulphonylamino (—$NHSO_2H$), $C_{1-6}$alkylsulphonylamino, e.g. methylsulphonylamino or ethylsulphonylamino, $C_{1-6}$dialkylsulphonylamino, e.g. dimethylsulphonylamino or diethylsulphonylamino, aminosulphonylamino (—$NHSO_2NH_2$), $C_{1-6}$alkylaminosulphonylamino, e.g. methylaminosulphonylamino or ethylaminosulphonylamino, $C_{1-6}$dialkylaminosulphonylamino, e.g. dimethylaminosulphonylamino or diethylaminosulphonylamino, $C_{1-6}$alkanoylamino, e.g. acetylamino, $C_{1-6}$alkanoylamino $C_{1-6}$alkyl, e.g. acetylaminomethyl or $C_{1-6}$alkoxycarbonylamino, e.g. methoxycarbonylamino, ethoxycarbonylamino or t-butoxycarbonylamino groups.

Where desired, two $R^{11}$ substituents may be linked together to form a cyclic group such as a cyclic ether, e.g. a $C_{2-6}$alkylenedioxy group such as ethylenedioxy.

It will be appreciated that where two or more $R^{11}$ substituents are present, these need not necessarily be the same atoms and/or groups. The $R^{11}$ substituents may be present at any ring carbon atom away from that attached to the rest of the molecule of formula (1). Thus, for example, in phenyl groups represented by $R^5$ any substituent may be present at the 2-, 3-, 4-, 5- or 6-positions relative to the ring carbon atom attached to the remainder of the molecule.

In the compounds of formula (1), when an ester group is present, for example a group —$CO_2Alk^2$ this may advantageously be a metabolically labile ester.

The presence of certain substituents in the compounds of formula (1) may enable salts of the compounds to be formed. Suitable salts include pharmaceutically acceptable salts, for example acid addition salts derived from inorganic or organic acids, and salts derived from inorganic and organic bases.

Acid addition salts include hydrochlorides, hydrobromides, hydroiodides, alkylsulphonates, e.g. methanesulphonates, ethanesulphonates, or isethionates, arylsulphonates, e.g. p-toluenesulphonates, besylates or napsylates, phosphates, sulphates, hydrogen sulphates, acetates, trifluoroacetates, propionates, citrates, maleates, fumarates, malonates, succinates, lactates, oxalates, tartrates and benzoates.

Salts derived from inorganic or organic bases include alkali metal salts such as sodium or potassium salts, alkaline earth metal salts such as magnesium or calcium salts, and organic amine salts such as morpheline, piperidine, dimethylamine or diethylamine salts.

Prodrugs of compounds of formula (1) include those compounds, for example esters, alcohols or aminos, which are convertible in vivo by metabolic means, e.g. by hydrolysis, reduction, oxidation or transesterification, to compounds of formula (1).

Particularly useful salts of compounds according to the invention include pharmaceutically acceptable salts, especially acid addition pharmaceutically acceptable salts.

In the compounds of formula (1), the group Y is preferably an —$OR^1$ group, especially where $R^1$ is an optionally substituted ethyl group or, especially, an optionally substituted methyl group. Especially useful substitutents which may be present on $R^1$ groups include one, two or three fluorine or chlorine atoms.

The group X in compounds of formula (1) is preferably —O—.

A particularly useful group of compounds of formula (1) has the formula (2):

where $R^2$ is an optionally substituted cycloalkyl group; $R^3$, $R^4$, $R^5$, $R^6$ and Z are as defined for formula (1); and the salts, solvates, hydrates and N-oxides thereof.

In the compounds of formulae (1) and (2) $R^2$ is preferably an optionally substituted cyclopentyl group. In particular, $R^2$ is a cyclopentyl group.

The group $R^3$ in compounds of formulae (1) or (2) is preferably a hydrogen atom or a $C_{1-3}$ alkyl group, particularly a methyl group.

In compounds of formulae (1) or (2) the group $R^4$ is preferably a hydrogen atom or a —CN or optionally substituted $C_{1-3}$ alkyl, especially a —$CH_3$ group.

Z in the compounds of formulae (1) or (2) is preferably —$(CH_2)_n$— where n is zero, 1 or 2. In particular, however, Z is especially —$(CH_2)_n$— where n is zero.

$R^5$ in the compounds of formulae (1) or (2) is preferably an optionally substituted phenyl group, particularly a phenyl group optionally substituted by one, two or more $R^{11}$ groups, and is especially a 2- or 3-monosubstituted or 2,6-disubstituted phenyl group. Particular substituents include halogen atoms, especially fluorine or chlorine atoms, and nitro, amino, alkoxy, haloalkyl, hydroxy, —$NHCOR^{8a}$, —$NHCONHR^{8a}$ and —$NHSO_2R^{8a}$ groups.

Particular $R^5$ groups include 2-nitrophenyl, 2-aminophenyl 2-haloalkylphenyl, e.g. 2-trifluoroalkylphenyl, 2-halophenyl, e.g. 2-fluorophenyl, 2-chlorophenyl, or 2-bromophenyl, 3-halophenyl, e.g. 3-fluorophenyl, 2,6-dihalophenyl, e.g. 2,6-difluorophenyl, or 2,6-dichlorophenyl, and 2,6-dialkoxyphenyl, e.g. 2,6-dimethoxyphenyl.

Other particularly useful $R^5$ groups in compounds of formulae (1) and (2) include 2-, 3- and 4-pyridinyl, thienyl, e.g. 2-thienyl or pyrimidinyl, especially 2-pyrimidinyl, groups, optionally substituted by one, two or more $R^{11}$ groups, especially halogen atoms, e.g. fluorine or chlorine atoms, nitro, amino, alkoxy, haloalkyl, hydroxy, —$NHCOR^{8a}$, —$NHCONHR^{8a}$ or —$NHSO_2R^{8a}$ groups.

Particularly useful groups of compounds of formulae (1) or (2) are those wherein $R^3$ is a hydrogen atom or a methyl group, $R^4$ is a hydrogen atom or a —CN or —$CH_3$ group and Z is a bond, and the salts, solvents, hydrates and N-oxides thereof. Especially useful compounds in groups of these types are those wherein $R^5$ is an optionally substituted phenyl, pyrimidinyl or pyridyl, e.g. 3- or 4-pyridyl, group. Particularly useful pyridyl groups of these types are 3,5-disubstituted-4-pyridyl and 3-monosubstituted -4-pyridyl.

$R^6$ in compounds of formula (1) or (2) is preferably a hydrogen atom.

Particularly useful compounds according to the invention are:

4-[2-(3-Cyclopentyloxy-4-methoxyphenyl)ethyl]pyridine;
3-Amino-4-[2-(3-Cyclopentyloxy-4-methoxyphenyl)ethyl] pyridine;
N-{4-[2-(3-Cyclopentyloxy-4-methoxyphenyl)ethyl]-3-pyridyl}phenyl-sulphonamide
(±)-3-(3-Cyclopentyloxy-4-methoxyphenyl)-2-(4-pyridyl) propanenitrile;
4-[2-(3-Cyclopentyloxy-4-methoxyphenyl)ethyl]-3,5-dichloropyridine;
4-[2-(3-Cyclopentyloxy-4-methoxyphenyl)ethyl)]-3-isobutylamidopyridine;
3-(3-Benzylureido)-4-[2-(3-cyclopentyloxy-4-methoxyphenyl)ethyl]pyridine; or
3-Benzamido-4-[2-(3-cyclopentyloxy-4-methoxyphenyl) ethyl]pyridine;

and the salts, solvates, hydrates and N-oxides thereof.

Compounds according to the invention are selective and potent orally active inhibitors of PDE IV. The ability of the compounds to act in this way may be simply determined by the tests described in the Examples hereinafter.

The compounds according to the invention are thus of particular use in the prophylaxis and treatment of human or animal diseases where an unwanted inflammatory response or muscular spasm (for example bladder or alimentary smooth muscle spasm) is present and where the elevation of cAMP levels may be expected to prevent or alleviate the inflammation and relax muscle.

Particular uses to which the compounds of the invention may be put include the prophylaxis and treatment of asthma, especially inflamed lung associated with asthma, cystic fibrosis, or in the treatment of inflammatory airway disease, chronic bronchitis, eosinophilic granuloma, psoriasis and other benign and malignant proliferative skin diseases, endotoxic shock, septic shock, ulcerative colitis, Crohn's disease, reperfusion injury of the myocardium and brain, inflammatory arthritis, chronic glomerulonephritis, atopic dermatitis, urticaria, adult respiratory distress syndrome, diabetes insipidus, allergic rhinitis, allergic conjunctivitis, vernal conjunctivitis, arterial restenosis and artherosclerosis.

Compounds of the invention also suppress neurogenic inflammation through elevation of cAMP in sensory neurones. They are, therefore, analgesic, anti-tussive and anti-hyperalgesic in inflammatory diseases associated with irritation and pain.

Compounds according to the invention may also elevate cAMP in lymphocytes and thereby suppress unwanted lymphocyte activation in immune-based diseases such as rheumatoid arthritis, ankylosing spondylitis, transplant rejection and graft versus host disease.

Compounds according to the invention have also been found to reduce gastric acid secretion and therefore can be used to treat conditions associated with hypersecretion.

Compounds of the invention suppress cytokine synthesis by inflammatory cells in response to immune or infectious stimulation. They are, therefore, useful in the treatment of bacterial, fungal or viral induced sepsis and septic shock in which cytokines such as tumour necrosis factor (TNF) are key mediators. Also compounds of the invention suppress inflammation and pyrexia due to cytokines and are, therefore, useful in the treatment of inflammation and cytokine-mediated chronic tissue degeneration which occurs in diseases such as rheumatoid or osteo-arthritis.

Over-production of cytokines such as TNF in bacterial, fungal or viral infections or in diseases such as cancer, leads to cachexia and muscle wasting. Compounds of the invention ameliorate these symptoms with a consequent enhancement of quality of life.

Compounds of the invention also elevate cAMP in certain areas of the brain and thereby counteract depression and memory impairment.

Compounds of the invention suppress cell proliferation in certain tumour cells and can be used, therefore, to prevent tumour growth and invasion of normal tissues.

For the prophylaxis or treatment of disease the compounds according to the invention may be administered as pharmaceutical compositions, and according to a further aspect of the invention we provide a pharmaceutical composition which comprises a compound of formula (1) together with one or more pharmaceutically acceptable carriers, excipients or diluents.

Pharmaceutical compositions according to the invention may take a form suitable for oral, buccal, parenteral, nasal, topical or rectal administration, or a form suitable for administration by inhalation or insufflation. Forms suitable for oral administration are particularly useful.

For oral administration, the pharmaceutical compositions may take the form of, for example, tablets, lozenges or capsules prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium hydrogen phosphate); lubricants (e.g. magnesium stearate, talc or silica); disintegrants (e.g. potato starch or sodium glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents, emulsifying agents, non-aqueous vehicles and preservatives. The preparations may also contain buffer salts, flavouring, colouring and sweetening agents as appropriate.

Preparations for oral administration may be suitably formulated for adult or pediatric use and/or to give controlled release of the active compound.

For buccal administration the compositions may take the form of tablets or lozenges formulated in conventional manner.

The compounds of formula (1) may be formulated for parenteral administration by injection e.g. by bolus injection or infusion. Formulations for injection may be presented in unit dosage form, e.g. in glass ampoule or multi dose containers, e.g. glass vials. The compositions for injection may take such forms as suspensions, solutions or emulsions in oily or aqueous vehicles, and may contain formulatory agents such as suspending, stabilising, preserving and/or dispersing agents. Alternatively, the active ingredient may be in powder form for constitution with a suitable vehicle, e.g. sterile pyrogen-free water, before use.

In addition to the formulations described above, the compounds of formula (1) may also be formulated as a depot preparation. Such long acting formulations may be administered by implantation or by intramuscular injection.

For nasal administration or administration by inhalation, the compounds for use according to the present invention are conveniently delivered in the form of an aerosol spray presentation for pressurised packs or a nebuliser, with the use of suitable propellant, e.g. dichlorodifluoromethane, trichlorofluoromethane, dichlorotetrafluoroethane, carbon dioxide or other suitable gas or mixture of gases.

The compositions may, if desired, be presented in a pack or dispenser device which may contain one or more unit dosage forms containing the active ingredient. The pack or dispensing device may be accompanied by instructions for administration.

The quantity of a compound of the invention required for the prophylaxis or treatment of a particular inflammatory condition will vary depending on the compound chosen, and the condition of the patient to be treated. In general, however, daily dosages may range from around 100 ng/kg to 100 mg/kg, e.g. around 0.01 mg/kg to 40 mg/kg body weight for oral or buccal administration, from around 10 ng/kg to 50 mg/kg body weight for parenteral administration and around 0.05 mg to around 1000 mg e.g. around 0.5 mg to around 1000 mg for nasal administration or administration by inhalation or insufflation.

The compounds according to the invention may be prepared by the following processes. The symbols Y, $R^2$, $R^3$, $R^4$, $R^5$, $R^6$, $R^7$ and X, when used in the formulae below are to be understood to represent those groups described above in relation to formula (1) unless otherwise indicated. In the reactions described below it may be necessary to protect reactive functional groups, for example hydroxy, amino, thio, or carboxy groups, where these are desired in the final product, to avoid their unwanted participation in the reactions. Conventional protecting groups may be used in accordance with standard practice [see, for example, Green, T. W. in "Protective Groups in Organic Synthesis" John Wiley and Sons, 1981.] It may be that deprotection will form the last step in the synthesis of compounds of formula (1). Thus, in one example, compounds of formula (1) wherein $R^4$ and/or $R^5$ contains a carboxylic acid group may be prepared by deprotecting the corresponding compound wherein $R^4$ and/or $R^5$ contains a protected carboxyl group, such as an oxazolinyl group, e.g. 4,4-dimethyl-2-oxazolinyl, in the presence of a base, e.g. sodium hydroxide, in an acid solvent e.g. aqueous hydrochloric acid, at an elevated temperature, e.g. the reflux temperature.

Thus according to a further aspect of the invention a compound of formula (1) wherein $R^3$ is as defined for formula (3) but is not a —CN or —CH$_2$CN group and $R^6$ is a hydrogen atom may be prepared by hydrogenation of a compound of formula (3):

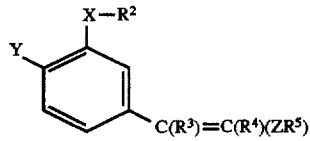

using for example hydrogen in the presence of a metal.

Suitable metals include for example platinum or palladium, optionally supported on an inert carrier such as carbon or calcium carbonate. The reaction may be performed in a suitable solvent, for example an alcohol such as ethanol or an ether such as tetrahydrofuran, optionally in the presence of a base, for example a tertiary organic base such as triethylamine, at for example ambient temperature.

Intermediates of formula (3) may be prepared by dehydration of an alcohol of formula (4)

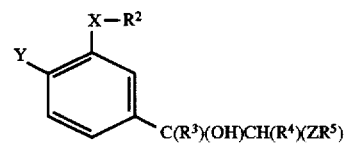

using an acid at an elevated temperature.

Suitable acids include for example phosphoric or sulphonic acids, e.g. 4-toluenesulphonic acid. The reaction may be performed in an inert organic solvent, for example a hydrocarbon such as toluene, at an elevated temperature, for example the reflux temperature.

It will be appreciated that alcohols of formula (4) are compounds of the invention in which the group R6 is a hydroxyl group. Thus according to a further aspect of the invention, a compound of formula (1) wherein $R^6$ is a hydroxyl group and $R^3$ is as defined for formula (1) but is not a —CN or —CH$_2$CN group may be prepared by reaction of a ketone or aldehyde of formula (5)

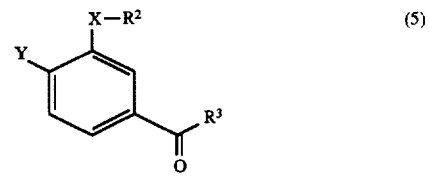

with an organometallic reagent $R^4R^5$ZCHM [where M is a metal atom, for example a lithium atom] in a solvent such as an ether, e.g. a cyclic ether such as tetrahydrofuran, at a low temperature e.g. around −70° C. to ambient temperature.

Reagents $R^4R^5$ZCHM are either known compounds or may be prepared, preferably in situ during the above process, by reaction of a compound AlkCH$_2$M or [Alk]$_2$NM [where Alk is an alkyl group such as a n-propyl or i-propyl group] with a compound $R^4R^5$ZCH$_2$ using the just mentioned reaction conditions.

Intermediates of formula (5) may be prepared by alkylation of a corresponding compound of formula (6)

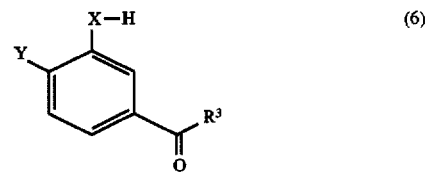

using a compound $R^2$Hal [where Hal is a halogen atom such as a bromine or chlorine atom] where necessary in the presence of a base such as caesium or potassium carbonate or an alkoxide such as potassium t-butoxide, in a diploar aprotic solvent such as an amide, e.g. a substituted amide such as dimethylformamide at ambient temperature or above e.g. around 40° C. to 50° C.

Intermediates of formula (5) are either known compounds or may be prepared from known starting materials by methods analogous to those used for the prepartion of the known compounds.

According to a still further aspect of the invention a compound of formula (1) wherein $R^6$ is a hydrogen atom may be prepared by alkylation of a compound of formula (7)

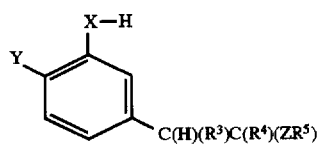

(7)

with a halide R²Hal, or with an alcohol R²OH.

The alkylation with the halide R²Hal may be performed using the reagents and conditions described above for the preparation of compounds of formula (6). Alkylation using an alcohol R²OH may be performed in the presence of a phosphine, such as triphenylphosphine, and an activator, for example diethyl azodicarboxylate, in the presence of an organic base such as triethylamine in a solvent such as tetrahydrofuran at an elevated temperature, e.g. the reflux temperature [see for example Mitsunobu, O., *Synthesis*, 1981, 1].

Intermediates of formula (7) may be prepared by reaction of an aldehyde or ketone of formula (6) with a compound R⁵ZCH₂R⁴ in the presence of a base or an acid in a suitable solvent.

Bases for use in this reaction include inorganic bases, for example alkali and alkaline earth metal bases, e.g. hydroxides, such as sodium or potassium hydroxide; alkoxides, for example sodium ethoxide, and organic bases, for example amines such as piperidine. Suitable solvents include alcohols such as ethanol. Acids for use in the reaction include organic acids, e.g. carboxylic acids such as acetic acid.

The reaction may be performed at any suitable temperature, for example from around ambient temperature to the reflux temperature depending on the nature of the starting materials.

In general, the base, acid, solvent and reaction conditions may be selected depending on the nature or the starting materials, from a range of known alternatives for reactions of this type.

In this reaction the group X-H may need to be in a protected state. Conventional hydroxy, amino or thiol protecting groups may be used in accordance with standard practice [see, for example, Green T. W., in "Protective Groups in Organic Synthesis" John Wiley and Sons, 1981].

Where an intermediate of formula (7) in which R³ is a —CN or —CH₂CN group is required this may be prepared by interconversion of a corresponding compound in which R³ is —CONH₂ or —CH₂CONH₂ as discussed below in relation to compounds of formula (1). Intermediates R⁵ZCH₂R⁴ are either known compounds or may be prepared from known starting materials by methods analogous to those used for the preparation of the known compounds.

Compounds of formula (1) may also be prepared by interconversion of other compounds of formula (1). Thus, for example, a substituted monocyclic or bicyclic aryl group R⁵ in compounds of formula (1) may be generally obtained by an appropriate substitution reaction using the corresponding unsubstituted compound of formula (1) and a R¹² containing nucleophile or electrophile. In another general process, a group R³ and/or R⁴ in formula (1) may be manipulated using conventional chemical procedures to yield other groups R³ and/or R⁴.

Thus in one example of an interconversion process a compound of formula (1) wherein R⁵ contains a —CH₂NH₂ substituent may be prepared by reduction of a corresponding compound wherein R⁵ contains a nitrile group, using for example a complex metal hydride such as lithium aluminium hydride in a solvent such as an ether e.g. diethylether.

In a further example, a compound of formula (1) wherein R⁵ contains a —NHCOR⁸ᵃ, —NHCONHR⁸ᵃ, —NHCON(R⁸ᵃ)₂, —NHCSR⁸ᵃ or alkanoylaminoalkyl substituent may be prepared by acylation or thiolation of a corresponding compound wherein R⁵ contains a —NH₂ or alkylamino group by reaction with an acyl halide e.g. an acyl chloride, an alkyl or aryl isocyanate, or a thiol halide in the presence of a base, such as a tertiary amine e.g. triethylamine or pyridine, optionally in a solvent such as dichloromethane.

In a still further example, a compound of formula (1) wherein R⁵ contains an alkoxy substituent may be prepared by alkylation of a corresponding compound wherein R⁵ contains a hydroxyl group by reaction with a compound AlkHal [where Alk is a C₁₋₆alkyl group such as a methyl or ethyl group and Hal is a halogen atom such as an iodine atom] in the presence of a base such as caesium or potassium carbonate in a dipolar aprotic solvent such as an amide, e.g. dimethylformamide at ambient temperature or above.

In another example a compound of formula (1) wherein R³ and/or R⁴ is a —CN or —CH₂CN group may be prepared by dehydration of a corresponding amide where R³ and/or R⁴ is —CONH₂ or —CH₂CONH₂ using for example trifluoroacetic anhydride in the presence of a base such as pyridine in a solvent such as tetrahydrofuran.

N-oxides of compounds of formula (1) may be prepared by oxidation of the corresponding nitrogen base using an oxidising agent such as hydrogen peroxide in the presence of an acid such as acetic acid, at an elevated temperature, for example around 70° C. to 80° C.

Salts of compounds of formula (1) may be prepared by reaction of a compound of formula (1) with an appropriate acid or base in a suitable solvent using conventional procedures.

Where it is desired to obtain a particular enantiomer of a compound of formula (1) this may be produced from a corresponding mixture of enantiomers using any suitable conventional procedure for resolving enantiomers. Thus for example diastereomeric derivatives, e.g. salts, may be produced by reaction of the mixture of enantiomers of formula (1) and an appropriate chiral compound e.g. a chiral acid or base. The diastereomers may then be separated by any convenient means for example by crystallisation and the desired enantiomer recovered, e.g. by treatment with an acid or base in the instance where the diastereomer is a salt. In another resolution process a racemate of formula (1) may be separated using chiral High Performance Liquid Chromatography.

The following examples illustrate the invention.
The following abbreviations are used:

| DMF | dimethylformamide |
|---|---|
| THF | tetrahydrofuran |
| DME | dimethoxyethane |
| EtOAc | ethyl acetate |
| Et₂O | diethylether |
| RT | room temperature |
| LDA | lithium diisopropylamide |

INTERMEDIATE 1

3-Cyclopentyloxy-4-methoxybenzaldehyde

Caesium carbonate (214 g, 0.66 mol) was added to a mixture of 3-hydroxy-4-methoxybenzaldehyde (1 00 g, 0.66 mol) and cyclopentyl bromide (98 g, 0.66 mol) in anhydrous DMF (50 ml). The reaction mixture was stirred at RT for 16 h then treated with a further portion of cyclopentyl bromide (98 g, 0.66 mol) and caesium carbonate (214 g, 0.66 mol). After a further 6 h at RT, the mixture was filtered and concentrated in vacuo. The residue was dissolved in dichloromethane (300 ml) and washed with sodium hydroxide solution (10%; 2×150 ml). The organic layer was dried (MgSO$_4$), concentrated in vacuo, and distilled (150° C., $10^{-2}$ mbar) to afford the title compound (130 g) as a viscous colourless oil. (Found: C, 70.38; H, 7.48. C$_{13}$H$_{16}$O$_3$ requires C, 70.89; H, 7.32%); δ$_H$ (CDCl$_3$) 1.5–2.0 (8H, br m, C H$_2$)$_4$), 3.87 (3H, s, OMe), 4.80 (1H, br m, OCHCH$_2$), 6.90 (1H, d, J 8.7 Hz, ArH ortho to OMe), 7.30–7.45 (2H, m, 2×ArH meta to OMe), and 9.77 (1H, s, ArCHO).

INTERMEDIATE 2

3,5- Dichloro-4-methylpyridine 3,5-Dichloropyridine (2.04 g, 13.5 mmol) in THF (5 ml) was added dropwise to a solution of LDA [prepared from diisopropylamine (1.9 ml, 13.5 mmol) and n-butyllithium (1.6M, 8.4 ml, 13.5 mmol)] in THF (25 ml) at −70° C. After stirring at this temperature for 5 min, iodomethane (0.85 ml, 13.5 mmol) was added and the reaction mixture stirred for a further 1.5 h at −70° C. Saturated sodium hydrogen carbonate solution (20 ml) and dichloromethane (20 ml) was added and the organic phase separated, dried (MgSO$_4$), and concentrated in vacuo. The residue was subjected to chromatography (SiO$_2$; Et$_2$O-hexane,1:3) to afford the title compound (1.16 g) as a pale yellow solid. δ$_H$ (CDCl$_3$) 2.46 (3H, s, Me), and 8.36 (2H, s, pyridine H$_2$, H$_6$).

INTERMEDIATE 3 a) (Z)-3-(3-Cyclopentyloxy-4-methoxyphenyl)-2-(2-pyridyl) propenenitrile

2-Pyridylacetonitrile (1.23 g, 11 mmol) and Intermediate 1 (2.20 g, 10 mmol) were dissolved in ethanol (3 ml) and added to a solution of sodium hydroxide (0.5 g) in water (4.5 ml). The reaction mixture was allowed to stir at RT for 2 h then partitioned between dichloromethane (20 ml) and saturated sodium hydrogen carbonate solution (15 ml). The organic layer was separated, dried (MgSO$_4$), and concentrated in vacuo to give the crude product. Trituration of the crude product with ethanol gave the title compound (2.40 g) as a yellow solid m.p. 82.5°–83° C. (Found: C, 78.87; H, 6.27; N, 8.46. C$_{20}$H$_{20}$N$_2$O$_2$ requires C, 74.98; H, 6.29; N, 8.74%); δ$_H$ (CDCl$_3$) 1.5–2.1 (8H, br m, (CH$_2$)$_4$), 3.824(3H, s, OMe), 4.80 (1H, br m, OCHCH$_2$), 6.84 (1H, d, J 8.6 Hz, ArH ortho to OMe), 7.05–7.25 (1H, m, pyridine H$_5$), (1H, dd, J 8.6, 1.95 Hz, ArH para to OMe), 7.6–7.75 (3H, m Ar H ortho to cyclopentyloxy+pyridine H$_3$,H$_4$), 8.29 (1H, s, C H=CCN) and 8.52 (1H, ca.d, J 4.6 Hz, pyridine H$_6$); m/z 320 (M$^+$, 15%), 252 (38), 251 (100), 237 (5), 236 (10), 209 (5), 179 (5), and 41 (8).

b) (Z)-3-(3-Cyclopentyloxy-4-methoxyphenyl)-2-(3-pyridyl) propenenitrile

Prepared in a similar manner to Intermediate 3 a) using 3-pyridylacetonitrile (2.35 ml, 22 mmol) and Intermediate 1 (4.40 g, 20 mmol). Chromatography (SiO$_2$; EtOAc) gave the title compound (5.31 g) as a pale yellow solid m.p. 86.5°–87.5° C. (Found: C, 74.80; H, 6.26; N, 8.74. C$_{20}$H$_{20}$N$_2$O$_2$ requires C, 74.98; H, 6.29; N, 8.74%); δ$_H$ (CDCl$_3$) 1.5–2.1 (8H, br m, (CH$_2$)$_4$), 3.87 (3H, s, OMe), 4.82 (1H, br m, OCHCH$_2$), 6.86 (1H, d, J 8.6Hz, ArH ortho to OMe), 7.2–7.4 (2H, m, ArH para to OMe+pyridine H$_3$), 7.42 (1H, s, CH=CCN), 7.70 (1H, d, J 2.0 Hz, ArH ortho to cyclopentyloxy), 7.87 (1H, dm, J 7.6 Hz, pyridine H$_4$), 8.53 (1H, dd, J 4.8, 1.3 Hz, pyridine H$_6$) and 8.84 (1H, d, J 2.4 Hz, pyridine H$_2$); m/z 320 (M$^+$, 20%), 252 (100), 251 (67), 234 (20), 223 (27), 205 (27), 151 (50), 69 (22), and 41 (31).

c) (Z)-3-(3-Cyclopentyloxy-4-methoxyphenyl-2-(4-pyridyl) propenenitrile

Prepared in a similar manner to Intermediate 3 c) using 4-pyridylacetonitrile (1.7 g, 11 mmol) and Intermediate 1 (2.20 g, 20 mmol). Trituration of the crude product with ethanol gave the title compound (2.75 g) as an orange solid m.p. 125°–127° C. (Found: C, 74.84; H, 6.29; N, 8.33. C$_{20}$H$_{20}$N$_2$O$_2$ requires C, 74.98; H, 6.29; N, 8.74%); δ$_H$ (CDCl$_3$) 1.5–2.1 (8H, br m, (CH$_2$)$_4$), 3.84 (3H, s, OMe), 4.83 (1H, br m, OCHCH$_2$), 6.83 (1H, d, J 8.2 Hz, ArH ortho to OMe), 7.26 (1H, dd, J 8.2, 2.2 Hz, ArH para to OMe), 7.44 (2H, dd, J 4.7, 1.7 Hz pyridine H$_3$,H$_5$), 7.53 (1H, s, C H=CCN) 7.69 (1H, d, J 2.2Hz, ArH ortho to cyclopentyloxy), 8.56 (2H, dd, J 4.7,1.5 Hz, pyridine H$_2$, H$_6$); m/z 320 (M$^+$, 28), 253 (19), 252 (100), 251 (59), 224 (15), 223 (38), 209 (10), and 41 (23).

d) (Z)-3-(3-Cyclopentyloxy-4-methoxyphenyl)-2-(2-naphthyl) propenenitrile

From 2-naphthylacetonitrile (1.67 g, 10 mmol) and Intermediate 1 (2.2 g, 10 mmol). The crude product was recrystallised from ethanol to afford the title compound (3.14 g) as a pale yellow solid. m.p. 147°–148° C. (Found: C, 81.15; H, 6.24; N, 3.56. C$_{25}$H$_{23}$NO$_2$ requires C, 81.27; H, 6.27; N, 3.79%); δ$_H$ (CDCl$_3$) 1.5–2.1 (8H, br m, (CH$_2$)$_4$), 3.88 (3H, s, OMe), 4.87 (1H, br m, OCHCH$_2$), 6.86 (1H, d, J 8.3 Hz, ArH meta to OMe), and 7.2–8.1 (10H, m, 2×ArH meta to OMe+CH=CCN+C$_{10}$H$_7$); m/z 370 (M$^+$+1, 10%), 369 (M$^+$, 40), 302 (23), 301 (100), 240 (20), 167 (12), 124 (38), and 41 (10).

INTERMEDIATE 4

(E)-4-[2-(3-Cyclopentyloxy-4-methoxyphenyl) ethenyl]-3-nitropyridine

A mixture of Intermediate 1 (2.13 g, 9.68 mmol), 4-methyl-3-nitropyridine (2.47 g, 17 mmol), and ammonium acetate (1.19 g, 15 mmol) in acetic acid (20 ml) was heated to reflux for 3 h. The reaction mixture was cooled and partitioned between dichloromethane (20 ml) and saturated sodium hydrogen carbonate solution (2×10 ml). The organic layer was separated, dried (MgSO$_4$), and concentrated in vacuo. The residue was subjected to chromatography (SiO$_2$; Et$_2$O-hexane, 1:1) to afford the title compound (1.83 g) as an orange solid m.p. 114°–116° C. (Found: C, 66.94; H, 5.94; N, 8.01. C$_{19}$H$_{20}$N$_2$O$_3$ requires C, 67.05; H, 5.92; N, 8.23%); δ$_H$ (CDCl$_3$) 1.5–2.1 (8H, br m, (CH$_2$)$_4$), 3.86 (3H, s, O Me), 4.75 (1H, br m, OCHCH$_2$), 6.84 (1H, d, J 8.5 Hz, Ar H ortho to OMe), 7.0–7.2 (2H, m, 2×ArH meta to OMe) 7.30 (1H, s, CH=CH), 7.38 (1H, s, CH=CH), 7.61 (1H, d, J 5.4 Hz, pyridine H$_5$), 8.73. (1H, d, J 5.4 Hz, pyridine H$_6$), and 9.09 (1H, s, pyridine H$_2$); m/z 340 (M$^+$, 15%) 308 (25), 240 (69), 226 (20), 225 (34), 152 (100), 151 (31), 149 (29), 121 (29), 68 (26), 67 (66), and 57 (22).

INTERMEDIATE 5 a) (E)-4-[2-(3-Cyclopentyloxy-4-methoxyphenyl) ethenyl]-3,5-dichloropyridine The compound of Example 1 a) (2.65 g, 6.92 mmol) was dissolved in toluene (60 ml) containing p-toluenesulphonic acid (0.2 g) and the mixture heated to reflux for 2.5 h in a Dean-Stark apparatus. The reaction mixture was concentrated in vacuo and the residue subjected to chromatography (SiO$_2$; Et$_2$O-hexane, 1:2) to afford the title compound (1.55 g) as yellow crystals m.p. 99°–101° C. (Found: C, 62.68; H, 5.22; N, 3.70. C$_{19}$H$_{19}$Cl$_2$NO$_2$ requires C, 62.65; H, 5.26; N, 3.85%); δ$_H$ (CDCl$_3$) 1.5–2.1 (8H, br m, (C$\underline{H}_2$)$_4$), 3.86 (3H, s, OM$\underline{e}$), 4.82 (1H, br m, OC$\underline{H}$CH$_2$), 6.83 (1H, d, J 8.9 Hz, Ar$\underline{H}$ ortho to OMe), 6.90 (1H, d, J 16.6 Hz, C$\underline{H}$=CH) 7.0–7.2 (2H, m, 2×Ar$\underline{H}$ meta to OMe) 7.40 (1H, d, J 16.6 Hz,C$\underline{H}$=CH), and 8.42(2H, s, pyridine $\underline{H}_2$, $\underline{H}_6$); m/z 365 (15%), 363 (20), 297 (67), 296 (28), 295 (100), 262 (29), 260 (79), 245 (36), 230 (22), 228 (27), 216 (23), and 152 (24).

The following compounds were prepared in a similar manner to Intermediate 5a.

b) (E)-2-[2-(3-Cyclopentyloxy-4-methoxyphenyl)ethenyl]pyridine

From the compound of Example 1b). The crude product was subjected to chromatography (SiO$_2$; Et$_2$O-hexane, 2:1) to afford the title compound (1.58 g) as a pale yellow solid m.p. 76°–77.5° C. (Found: C, 77.20; H, 7.20; N, 4.63. C$_{19}$H$_{21}$NO$_2$ requires C, 77.26; H, 7.17; N, 4.74%); δ$_H$ (CDCl$_3$) 1.5–2.1 (8H, br m, (C$\underline{H}_2$)$_4$), 3.84 (3H, s, OM$\underline{e}$), 4.80 (1H, br m, OC$\underline{H}$), 6.80 (1H, d, J 8.5Hz, Ar$\underline{H}$ orthoto OMe), 6.95 (1H, d, J 15.6 Hz,C$\underline{H}$=CH), 6.95–7.7 (5H, m, 2×Ar$\underline{H}$ meta to OMe+pyridine $\underline{H}_3$, $\underline{H}_4$, $\underline{H}_5$), 7.51 (1H, d, J 1656 Hz, CH=C$\underline{H}$), and 8.53(1H, dm, J 4.9 Hz, pyridine $\underline{H}_6$); m/z 295 (M$^+$, 23%), 294 (11), 227 (21), 226 (100), 211 (18), 184 (10), and 154 (13).

c) (E)-4-[2-(3-Cyclopentyloxy-4-methoxyphenyl)-1-propenyl]pyridine

From Intermediate 8 (1 g) Chromatography (SiO$_2$; dichloromethane) followed by recrystallisation (hexane) afforded a mixture of (Z)- title compound, 4-{2-[1-(3-Cyclopentyloxy-4-methoxyphenyl)propenyl]pyridine, and the title compound (247 mg) as white needles m.p. 78°–79° C. Found C, 77.64; H, 7.58; N, 4.41 C$_{20}$H$_{23}$NO$_2$ requires C, 77.63; H, 7.49; N, 4.52%). δ$_H$ (80 MHz; CDCl$_3$) 1.6–2.0 (8H, br m, (C$\underline{H}_2$)$_4$), 2.26 (3H, d, J 1.3 Hz, C$\underline{H}_3$), 3.85 (3H, s, OM$\underline{e}$), 4.75–4.85 (1H, m, OC$\underline{H}$CH$_2$), 6.60–7.21 (6H, m, Ar$\underline{H}$+Py$\underline{H}_3$, $\underline{H}_5$+C=C$\underline{H}$), and 8.52 (2H, br d, PY$\underline{H}_2$, $\underline{H}_6$). m/z (EI) 309 (M$^+$, 30%), 241 (100), 222 (21), and 212 (29).

d) (E)-312-(3-Cyclopentyloxy-4-methoxyphenyl)ethyl]-2-methoxy-pyrazine

From Example 2d (3.9 g). Chromatography (SiO$_2$; Et$_2$O-hexane, 1:1) followed by recrystallisation (i-propanol-hexane, 1:1 ) afforded the title compound (3.24 g) as a yellow solid m.p. 71.73° C.

INTERMEDIATE 6 a) (E)-4-[2-(3-Cyclopentyloxy-4-methoxyphenyl)ethenyl]pyridazine

The compound of Example 2a) was dissolved in toluene (50 ml) containing 4-toluenesulphonic acid (0.1 g) and the mixture heated to reflux in a Dean-Stark apparatus for 2 h. The cooled reaction mixture was poured into saturated sodium hydrogen carbonate solution (25 ml) and extracted with dichloromethane (1×50 ml, 1×25 ml). The organic extract was dried (MgSO$_4$), concentrated in vacuo and the residue subjected to chromatography (SiO$_2$; Et$_2$O-hexane, 1:1) to afford the title compound (370 mg) (Found: C, 72.75; H, 6.78; N, 9.23. C$_{18}$H$_{20}$N$_2$O$_2$ requires C, 72.95; H, 6.80; N, 9.45%); δ$_H$ (CDCl$_3$) 1.5–2.1 (8H, br m, (C$\underline{H}_2$)$_4$), 3.85 (3H, s, OM$\underline{e}$), 4.82 (1H, br m, OC$\underline{H}$), 6.75–7.7 (7H, br m, Ar$\underline{H}$ ortho to OMe+2×Ar$\underline{H}$ meta to OMe+C$\underline{H}$=C$\underline{H}$+pyridazine $\underline{H}_3$, $\underline{H}_5$), 8.95 (1H, dd, J 4.3, 1.4 Hz, pyridazine $\underline{H}_6$).

b) (E)-4-[2-(3-Cyclopentyloxy-4-methoxyphenyl)ethenyl]pyridine

Prepared in a similar manner to Intermediate 6a) using the compound of Example 2b). The crude product was subjected to chromatography (SiO$_2$; EtOAc) to afford the title compound (7.47 g) as pale yellow needles m.p. 108°–108.5° C. (from Et$_2$O-hexane). (Found: C, 76.92; H, 7.12; N, 4.88. C$_{19}$H$_{21}$NO$_2$ requires C, 77.26; H, 7.17; N, 4.74%); δ$_H$ (CDCl$_3$) 1.5–2.1 (8H, br m, (C$\underline{H}_2$)$_4$), 3.84 (3H, s, OM$\underline{e}$), 4.81 (1H, br m, OC$\underline{H}$CH$_2$), 6.77 (1H, d, J 15.8 Hz, C$\underline{H}$=CH), 6.81 (1H, d, J ca. 9 Hz, Ar$\underline{H}$ ortho to OMe), 6.95–7.1 (3H, m, Ar$\underline{H}$ meta to OMe+CH=C$\underline{H}$), 7.28 (2H, dd, J 4.7, 1.6 Hz, pyridine $\underline{H}_3$, $\underline{H}_5$), and 8.49 (2H, dd, J 4.7, 1.6 Hz, pyridine $\underline{H}_2$, $\underline{H}_6$); m/z 295 (M$^+$, 35%), 228 (20), 227 (100), 226 (86), 198 (34), 184 (23), 167 (12), 166 (16), 154 (10), and 41 (20).

c) (E)-2-[2-(3-Cyclopentyloxy-4-methoxyphenyl)ethenyl]pyrazine

Prepared in a similar manner to Intermediate 6a) using the compound of Example 2c). The crude product was subjected to chromatography (SiO$_2$; ether-hexane, 1:1) to afford the title compound (0.80 g) as a pale brown solid m.p. 81°–83° C. (Found: C, 72.94; H, 6.78; N, 9.23. C$_{18}$H$_{20}$N$_2$O$_2$ requires C, 72.94; H, 6.80; N, 9.45%); δ$_H$ (CDCl$_3$) 1.5–2.0 (8H, br m, (C$\underline{H}_2$)$_4$), 3.84 (3H, s, OM$\underline{e}$), 4.80 (1H, br m, OC$\underline{H}$), 6.81 (1H, d, J 8.8 Hz, Ar$\underline{H}$ ortho to OMe), 6.93 (1H, d, J 15.9 Hz, C$\underline{H}$=CH), 7.0–7.15 (2H, m, 2×Ar$\underline{H}$ meta to OMe) 7.63 (1H, d, J 15.9 Hz, CH=C$\underline{H}$), and 8.25–8.60 (3H, m, pyrazine $\underline{H}_3$, $\underline{H}_5$, $\underline{H}_6$).

INTERMEDIATE 7

(3-Cyclopentylpxy-4-methoxy)phenyl methyl ketone

To a solution of methylmagnesiumbromide (5.44 ml) in THF (150 ml) at 10° C. was added Intermediate 1. The reaction mixture was left to stir at RT for 5–6 hr, then NH$_4$Cl and Et$_2$O (100 ml) were added and the solution stirred for another 90 min (the solution went from hazy to clear). The layers were separated, the aqueous layer was extracted with Et$_2$O (50 ml) the combined organic layer was extracted with a saturated bicarbonate solution (100 ml) then brine (100 ml). Evaporation in vacuo afforded 1-methoxy-2-cyclopentyloxy-4-(1-hydroxyethyl)benzene which was disolved in dichloromethane (300 ml) before adding MnO$_2$ (10 eq). The reaction mixture was stirred for 120 h, then the MnO$_2$ was filtered off and the solvent evaporation in vacuo. Purification by column chromatography (SiO$_2$; dichloromethane-hexane, 350–150 to dichloromethane) afforded the title compound.

INTERMEDIATE 8

4-[2-(3-Cyclopentyloxy-4-methoxyphenyl)-2-methyl-2-hydroxyethyl]pyridine

To a cold (−78° C.) solution of 4-picoline (0.80 ml) in THF was added n-BuLi (5.6 ml), the solution stirred for 30 min then transferred to a cold suspension of cerium chloride anhydrous (2.0 g) at −78° C. The reaction mixture was stirred for 1 h before adding Intermediate 7 in THF then left to warm to RT overnight. 10% NH$_4$Cl solution and EtOAc were added, the solution was filtered through Celite, washed with EtOAC (150 ml) and the organic layer was separated, washed with brine (100 ml) then dried (Na$_2$SO$_4$). The solvents were evaporated in vacuo to afford the title compound (2.367 g) as pale off-white crystals m.p. 99°–101° C. Found C, 73.21; H, 7.63; N, 4.20. C$_{20}$H$_{25}$NO$_3$ requires C 73.37; H, 7.70; N, 4.28%). m/z (EI) 327 (M$^+$, 3%), 235 (18), 166 (38), 151 (100), and 93 (54).

EXAMPLE 1 a) (±)-4-[2-(3-Cyclopentyloxy-4-methoxyphenyl)-2-hydroxyethyl]-3,5-dichloropyridine Intermediate 2 (2.22 g, 13 mmol) in THF (40 ml) was added dropwise to a solution of LDA [prepared from diisopropylamine (2.4 ml, 17 mmol) and n-butyllithium (1.6M, 10.2 ml, 16 mmol)] in THF (50 ml) at −70° C. and the mixture stirred at this temperature for 0.25 h. A solution of Intermediate 1 (3.32 g, 15 mmol) in THF (50 ml) was then added at −70° C. and the reaction mixture allowed to warm to RT overnight. Saturated ammonium chloride solution (50 ml) and dichloromethane (50 ml) was added and the organic phase separated, dried (MgSO$_4$), and concentrated in vacuo. The residual yellow solid was triturated with hot Et$_2$O to afford the title compound (2.65 g) as a white solid m.p. 139°–140° C. (Found: C, 59.49; H, 5.68; N, 3.57. C$_{19}$H$_{21}$Cl$_2$NO$_3$ requires C, 59.69; H, 5.53; N, 3.66%); δ$_H$ (CDCl$_3$) 1.5–2.1 (8H, br m, CH$_2$)$_4$), 3.81 (3H, s, OMe), 4.7 (1H, br m, OCHCH$_2$), 5.01 (1H, dd J 5.8, 8.4 Hz, CHOH), 6.75–6.9 (3H, m, ArH ortho to OMe+2×ArH meta to OMe), and 8.36 (2H, s, pyridine H$_2$, H$_6$); m/z 383 (10%), 381 (17), 221 (46), 163 (49), 161 (74), 153 (100), 152 (24), 151 (17), 125 (27), 93 (48), 65 (25), and 41 (34).

The following compounds were prepared in a similar manner to the compound of Example 1 a.

b) (±)-2-[2-(3-Cyclopentyloxy-4-methoxyphenyl)-2-hydroxyethyl]pyridine

From 2-methylpyridine (1.02 g, 11 mmol), LDA (1.0 equiv), and Intermediate 1 (2.45 g, 11 mmol). The crude product was subjected to chromatography (SiO$_2$; Et$_2$O) to afford the title compound (2.67 g) as a yellow solid m.p. 94°–96° C. (Found: C, 72.89; H, 7.43; N, 4.58. C$_{19}$H$_{23}$NO$_3$ requires C, 72.82; H, 7.40; N, 4.47%); δ$_H$ (CDCl$_3$) 1.5–2.1 (9H, br m, (CH$_2$)$_4$+OH), 3.09 (2H, d, J 6.1 Hz, CH$_2$Ar), 3.80 (3H, s, OMe), 4.74 (1H, br, d, OCHCH$_2$), 5.06 (1H, t, J 6.1Hz, CHOH), 6.8–7.2 (5H, m, ArH ortho to OMe+2×Ar H meta to OMe+pyridine H$_3$, H$_4$), 7.56 (1H, m, pyridine H$_5$) and 8.47 (1H, dm, J 4.5Hz, pyridine H$_6$); m/z 313 (M$^+$, 5%), 153 (16), 152 (90), 151 (53) 93 (100), 80 (17), and 41 (14).

c) (±)-4-[2-(3-Cyclopentyloxy-4-methoxyphenyl)-2-hydroxyethyl]pyrimidine

From 4-methylpyrimidine (2.15 g, 23.6 mmol), LDA (1.0 equiv), and Intermediate 1 (5.12 g, 23.0 mmol). The crude product was subjected to chromatography (SiO$_2$; Et$_2$O) to afford the title compound (3.83 g) as an amber oil. (HCl salt m.p. 211°–213° C.) (HCl salt Found: C, 62.24; H, 6.68; N, 8.06. C$_{18}$H$_{23}$N$_2$O$_3$ requires C, 61.44; H, 6.87; N, 7.96%); δ$_H$ (CDCl$_3$) 1.5–2.1 (8H, br m, (CH$_2$)$_4$), 3.10 (2H, d, J 6.5 Hz, CH$_2$Ar), 3.80 (3H, s, OMe), 4.15 (1H, br, s OH), 4.74 (1H, br, m, OCHCH$_2$), 5.10 (1H, t, J 6.5Hz, CHOH), 6.75–6.9 (3H, m, ArH ortho to OMe+2×ArH meta to OMe), 7.09 (1H, dd, J 4.9 Hz, pyrimidine H$_5$), 8.53 (1H, d, J 4.9 Hz, pyrimidine H$_6$), and 9.07 (1H, d, J 4.0Hz, pyrimidine H$_2$); m/z 314 (M$^+$, 16%), 296 (19), 228 (23), 227 (75), 166 (18), 153 (22), 152 (20), 151 (16), 94 (100), and 41 (26).

EXAMPLE 2 a) (±)-4-[2-(3-Cyclopentyloxy-4-methoxyphenyl)-2-hydroxyethyl]pyridazine n-Butyllithium (1.6M in hexanes) (9.5 ml, 6.0 mmol) was added dropwise to a solution of methylpyridazine (0.47 g, 5.0 mmol) in THF (25 ml) at −70° C. The reaction mixture was allowed to stir at this temperature for 0.5 h then a solution of Intermediate 1 (1.1 g, 5.0 mmol) in THF (20 ml) was added. The mixture was allowed to warm to RT then partitioned between dichloromethane (25 ml) and saturated sodium hydrogen carbonate solution (25 ml). The organic phase was separated, dried (MgSO$_4$), and concentrated in vacuo to afford the title compound.

The following compounds were prepared in a similar manner to the compound of Example 2a.

b) (±)-4-[2-(3-Cyclopentyloxy-4-methoxyphenyl)-2-hydroxyethyl]pyridine

From 4-methylpyridine (3.00 g, 32.1 mmol), n-butyllithium (32.1 mmol), and Intermediate 1 (6.82 g, 31.0 mmol). The crude product was subjected to chromatography [SiO$_2$; EtOAc-hexane, 3:2 (500 ml) to 4:1 (1000 ml) then EtOAc-methanol, 9:1 (1 500 ml)] to afford the title compound (9.68 g) as fine white needles m.p. 97°–101° C. (from toluene). δ$_H$ (CDCl$_3$) 1.5–2.0 (8H, br m, (CH$_2$)$_4$), 2.45(1H, br, s, CHOH), 2.96 (2H, d, J 6.5 Hz, CH$_2$ pyridine), 3.80 (3H, s, OMe), 4.70 (1H, br, m, OCHCH$_2$), 4.81 (1H, t, J 6.5 Hz, CHOH), 6.76(3H, s, ArH ortho to OMe+2×ArH meta to OMe), 7.00 (2H, dm, J 4.5 Hz, pyridine H$_3$, H$_5$), and 8.33 (2H, dm, J 4.5Hz, pyridine H$_2$, H$_6$).

c) (±)-2-[2-(3-Cyclopentyloxy-4-methoxyphenyl)-2-hydroxyethyl]pyrazine

From methylpyrazine (0.94 g, 11 mmol), n-butyllithium (1.6M; 6.9 ml, 11 mmol), and intermediate 1 (2.2 g, 10 mmol) to afford the title compound as a yellowish oil.

d) (±)-3-[2-(3-Cyclopentyloxy-4-methoxyphenyl)-2-hydroxyethyl]-2-methoxypyrazine From 2-methoxy-3-methylpyrazine (1.76 ml, 15 mmol), Intermediate 1 (3.3 g, 15 mmol) and n-butyllithium (10.62 ml, 17 mmol). Chromatography (SiO$_2$; EtOAc) afforded the title compound (4.473 g).

EXAMPLE 3 a) 3-Amino-4-[2-(3-cyclppentyloxy-4-methoxyphenyl)ethyl]pyridine

A solution of Intermediate 4 (2.178 g) in THF (50 ml) was hydrogenated over Pd/C (10%; 20 mg) at RT. The reaction mixture was filtered through Celite® and the filtrate concentrated in vacuo. The residue was recrystallised from Et$_2$O to afford the title compound (1.95 g) as a white solid m.p. 108°–110.5° C. (Found: C, 72.55; H, 7.66; N, 8.82. C$_{19}$H$_{24}$N$_2$O$_2$ requires C, 73.04; H, 7.74; N, 8.97%); δ$_H$ (CDCl$_3$) 1.5–2.0 (8H, br m, (CH$_2$)$_4$), 2.74–2.85 (4H, br, m, CH$_2$CH$_2$Ar), 3.4 (2H, br m, NH$_2$), 3.79 (3H, s, OMe), 4.64 (1H, br, m, OCH), 6.61 (1H, d, J 2.0 Hz, ArH ortho to cyclopentyloxy), 6.68 (1H, dd, J 8.1, 2.0 Hz, ArH para to cyclopentyloxy), 6.78 (1H, d, J 8.1 Hz, ArH ortho to OMe), 6.85 (1H, d, J 5.1 Hz, pyridine H$_5$), 7.90 (1H, d, J 5.1 Hz, pyridine H$_6$), and 7.94 (1H, s, pyridine H$_2$); m/z 312 (M$^+$, 51%), 244 (78), 243 (42), 205 (27), 138 (40), 137 (100), 122 (24), 109 (35), 108 (100), 107 (24), and 41 (24).

The following compounds were prepared in a similar manner to the compound of Example 3a.

b) (±)-3-(3-Cyclopentyloxy-4-methoxyphenyl)-2-(2-pyridyl)-propanenitrile

From Intermediate 3a) (800 mg) in methanol (100 ml) to afford the title compound (756 mg) as a yellow solid; δ$_H$ (CDCl$_3$) 1.5–2.0 (8H, br m, (CH$_2$)$_4$), 3.21 (2H, d, J 7.9 Hz, CH$_2$CHCN), 3.78 (3H, s, OMe), 4.14 (1H, t, J 7.9 Hz, CH$_2$C HCN), 4.70 (1H, br m, OCH), 6.6–6.75 (3H, m) and 7.15–7.3 (2H, m) (C$_6$H$_3$+pyridine H$_3$, H$_4$), 7.60 (1H ca. dt, J ca. 7.5, 2 Hz, pyridine H$_5$), 8.56 (1H, dm, J ca 5 Hz, pyridine H$_6$); m/z 322 (M$^+$, 12%), 296 (15), 254 (30), 228 (10), 138 (18), 137 (100), 79 (10), and 41 (10).

c) (±)-3-(3-Cyclopentyloxy-4-methoxyphenyl)-2-(3-pyridyl)propanenitrile

From Intermediate 3 b) (500 mg) in methanol (15 ml) to afford the title compound (420 mg) as a colourless oil; δ$_H$ (CDCl$_3$) 1.6–2.0 (8H, br m, (CH$_2$)$_4$), 3.07 (2H, d, J 7.1 Hz, CH$_2$CHCN), 3.76 (3H, s, OMe), 3.99 (1H, t, J 7.1 Hz, CH$_2$C HCN), 4.70 (1H, br m, OCH), 6.5–6.75 (3H, m) and 7.2–7.45 (2H, m) (2×ArH meta to OMe+ArH ortho to OMe+pyridine H$_4$, H$_5$), and 8.35–8.55 (2H, m, pyridine H$_2$, H$_6$); m/z 322 (M$^+$, 22%), 254 (51), 205 (38), 138 (76), 137 (100), 122 (34), 118 (16), 94 (16), 85 (16), 65 (15), and 41 (38).

d) (±)-3-(3-Cyclopentyloxy-4-methoxyphenyl)-2-(4-pyridyl)propanenitrile

From Intermediate 3 c) (800 mg) in methanol (100 ml) to afford the title compound (712 mg) as a yellow oil; δ$_H$ (CDCl$_3$) 1.5–2.0 (8H, br m, (CH$_2$)$_4$), 3.08 (2H, d, J 7.1 Hz, CH$_2$CHCN), 3.79 (3H, s, OMe), 3.96 (1H, t, CH$_2$CHCN), 4.65 (1H, br m, OCH), 6.5–6.8 (3H, m, 2×ArH meta to OMe+ArH ortho to OMe), 7.10 (2H, dd, J 4.5, 1.8 Hz, pyridine H$_3$, H$_5$), and 8.45 (2H, dd, J 4.5, 1.8 Hz pyridine H$_2$, H$_6$); m/z 322 (M$^+$, 5%), 254 (13), 229 (10), 138 (13), 137 (100), 85 (15), and 41 (12).

e) 2-[2-(3-Cyclopentyloxy-4-methoxyphenyl)ethyl] pyridine

From Intermediate 5 b) (0.72 g) to afford the title compound (0.68 g) as a pale yellow oil. (Found: C, 76.23; H, 7.79; N, 4.52. C$_{19}$H$_{23}$NO$_2$ requires C, 76.74; H, 7.80; N, 4.71%); δ$_H$ (CDCl$_3$) 1.5–2.0 (8H, br m, (CH$_2$)$_4$), 2.9–3.1 (4H, m, CH$_2$CH$_2$Ar), 3.81 (3H, s, OMe), 4.70 (1H, br, m, OCH), 6.65–6.8 (3H, m) and 7.0–7.15 (2H, m) (pyridine H$_3$, H$_4$ and C$_6$H$_3$), 7.55 (1H, dt, J 7.6, 1.8 Hz, pyridine H$_5$) and 8.56 (1H, dm J~5 Hz, pyridine H$_6$); m/z 297 (M$^+$, 27%), 229 (60), 228 (51), 214 (39), 138 (13), 137 (100), 106 (17), 94 (12), 93 (53), and 41 (20).

f) 4-[2-(3-Cyclopentyloxy-4-methoxyphenyl)ethyl] pyridine

From Intermediate 6 b) (700 mg) in methanol (100 ml) containing a few drops of triethylamine to afford the title compound (685 mg) (Found: C, 76.55; H, 7.88; N, 4.89. C$_{19}$H$_{23}$NO$_2$ requires C, 76.48; H, 8.10; N, 4.69%).

g) 2-[2-(3-Cyclopentyloxy-4-methoxyphenyl)ethyl] pyrazine

From Intermediate 6 c) (700 mg) in methanol (100 ml) to afford the title compound (680 mg) as yellow crystals. (Found: C, 72.36; H, 7.47; N, 9.17. C$_{18}$H$_{22}$N$_2$O$_2$ requires C, 72.46; H, 7.43; N, 9.39%); δ$_H$ (CDCl$_3$) 1.4–2.0 (8H, br m, (CH$_2$)$_4$), 2.95–3.1 (4H, m, CH$_2$CH$_2$Ar), 3.78 (3H, s, OMe), 4.67 (1H, br, m, OCH), 6.5–6.7 (3H, m, 2×ArH meta to OMe+ArH ortho to OMe) and 8.3–8.5 (3H, m, pyrazine H$_3$, H$_5$, H$_6$).

h) 3-[2-(3-Cyclopentyloxy-4-methoxyphenyl)ethyl]-2-methoxy-pyrazine

From Intermediate 5d (770 mg) in methanol (100 ml) to afford the title compound (700 mg) as a colourless oil (Found: C, 69.51; H, 7.39; N, 8.45. C$_{19}$H$_{24}$N$_2$O$_3$ requires C, 69.49; H, 7.37; N, 8.53%); δ$_H$ (CDCl$_3$) 1.4–2.0 (8H, br m, (CH$_2$)$_4$), 2.9–3.1 (4H, m, CH$_2$CH$_2$Ar), 3.78 (3H, s, OMe), 3.92 (3H, s, OMe), 4.70 (1H, br, m, OCH), 6.72 (3H, s, 2×Ar H meta to OMe+ArH ortho to OMe), 7.87 (1H, d, J 2.8 Hz) and 7.98 (1 H, d, J 2.8 Hz), (pyrazine H$_5$, H$_6$); m/z 338 (M$^+$, 31%), 271 (11), 270 (63), 205 (40), 137 (100), and 122 (9).

i) 4-[2-(3-Cyclopentyloxy-4-methoxyphenyl)propyl] pyridine

From a mixture of the three stereoisomers described in Intermediate 5c (0.9 g). Chromatography (SiO$_2$; EtOAc) afforded the title compound (0.696 g) as a clear oil. (Found C, 76.88; H, 8.07; N, 4.36. C$_{20}$H$_{25}$NO$_2$ requires C, 77.14; H, 8.09; N, 4.50). δ$_H$ (CDCl$_3$) 1.26 (3H, ca. d, J 6.3 Hz CH Me), 1.5–2.0 (8H, br m, (CH$_2$)$_4$), 2.7–2.9 (3H, m, MeC HCH$_2$), 3.78 (3H, s, OMe), 6.55–6.8 (3H, m, C$_6$H$_3$), 6.89 (2H, dm, J ca 4.5Hz, pyridine H$_3$, H$_5$), and 8.36 (2H, dm, J ca 4.5 Hz, pyrodome H$_2$ H$_6$); m/z (EI) 311 (M$^+$, 29%), 243 (100), 242 (23), 219 (58), 151 (86), and 91 (18).

j) (±)-3-(3-Cyclopentyloxy-4-methoxy)phenyl-2-(2-naphthyl)propanenitrile

From Intermediate 3d (1.5 g). Filtration through celite followed by concentration in vacuo afforded the title compound (0.351 g) as a white solid. m.p. 134°–135° C. (Found C, 80.852; H, 6.808; N, 3.822. C$_{25}$H$_{23}$NO$_2$ requires C, 80.832; H, 6.783; N, 3.77%). m/z 371 (18%), 137 (100), and 205 (96).

EXAMPLE 4 a) 3-Benzamido-4-[2-(3-cyclopentyloxy-4-methoxyphenyl)ethyl]pyridine

Benzoyl chloride (0.13 ml, 1.0 mmol) was added to a solution of the compound of Example 3 a) (263 mg, 0.88 mmol) in pyridine (10 ml) and the reaction mixture allowed to stir at RT for 18 h. The mixture was concentrated in vacuo and the residue was subjected to chromatography (SiO$_2$; EtOAc) to afford the title compound (237 mg) as a white foam m.p. 50°–51° C. (Found: C, 74.44; H, 6.79; N, 6.69. C$_{26}$H$_{28}$N$_2$O$_3$ requires C, 74.97; H, 6.77; N, 6.77%); δ$_H$ (CDCl$_3$) 1.5–1.9 (8H, br m, (CH$_2$)$_4$), 2.90 (4H, br, s, C H$_2$CH$_2$Ar), 3.78 (3H, s, OMe), 4.48 (1H, br, m, OCH), 6.43 (1H, d, J 2.0 Hz ArH ortho to cyclopentyloxy), 6.57 (1H, dd, J 8.1, 2.0 Hz, ArH para to cyclopentyloxy), 6.74 (1H, d, J 8.1Hz, ArH ortho to OMe), 6.93 (1H, br s, NHCO), 7.22 (1H, d, J 5.0 Hz, pyridine H$_5$), 7.4–7.65 (5H, m, C$_6$H$_5$), 8.42 (1H, d, J 5.0 Hz, pyridine H$_6$) and 8.81 (1H, s, pyridine H$_2$); m/z 416 (M$^+$, 14%), 349 (22), 348 (100), 347 (26), 212 (17), 199 (18), 137 (93), 105 (90), and 77 (38).

The following compounds were prepared in a manner similar to the compound of Example 48.

b) 4-[2-(3-Cyclopentyloxy-4-methoxyphenyl)ethyl]-3-methylamido-pyridine

From the compound of Example 3 a) (309 mg, 1.0 mmol) and acetyl chloride (0.1 ml, 1.4 mmol) to afford the title compound (276 mg) as white crystals. $\delta_H$ (CDCl$_3$) 1.5–2.0 (8H, br m, (C$\underline{H}_2$)$_4$), 1.96 (3H, s, NHCO$\underline{Me}$), 2.85 (4H, s, C$\underline{H}_2$CH$_2$Ar), 3.82 (3H, s, O$\underline{Me}$), 4.59 (1H, br, s, OC$\underline{H}$), 6.18 (1H, br s, N$\underline{H}$COMe), 6.46 (1H, d, J 2.0 Hz, Ar$\underline{H}$ ortho to cyclopentyloxy), 6.63 (1H, dd, J 8.1, 2.0 Hz, Ar$\underline{H}$ para to cyclopentyloxy), 6.81 (1H, d, J 8.1 Hz, Ar$\underline{H}$ ortho to OMe), 7.15 (1H, d, J 4.9 Hz, pyridine $\underline{H}_5$), 8.36 (1H, br d, J ca 4.6 Hz, pyridine $\underline{H}_6$), and 8.70 (1H, br s, pyridine $\underline{H}_2$); m/z 354 (M$^+$, 8%), 286 (50), 285 (16), 151 (27), 150 (47), 138 (17), 137 (100), 122 (10), 119 (11), 43 (17), and 41 (17).

c) 4-[2-(3-Cyclopentyloxy-4-methoxyphenyl)ethyl]-3-isobutylamido-pyridine

From the compound of Example 3 a) (450 mg, 1.5 mmol) and isobutyryl chloride (0.22 ml, 2.1 mmol) to afford the title compound (310 mg) as a white solid m.p. 100°–101.5° C. (Found: C, 72.01; H, 7.90; N, 7.26. C$_{23}$H$_{30}$N$_2$O$_3$ requires C, 72.22; H, 7.90; N, 7.32%); $\delta_H$ (CDCl$_3$) 1.15 (6H, d, J 6.9 Hz, CH$\underline{Me}_2$), 1.1–1.8 (8H, br m, (C$\underline{H}_2$)$_4$), 2.26(1H, m, C$\underline{H}$Me$_2$), 2.84 (4H, s, C$\underline{H}_2$C$\underline{H}_2$Ar), 3.81 (3H, s, O$\underline{Me}$), 4.58 (1 H, br, m, OC$\underline{H}$), 6.22 (1H, br s, N$\underline{H}$CO), 6.44 (1H, d, J 2.0 Hz Ar$\underline{H}$ ortho to cyclopentyloxy), 6.62 (1H, dd, J 8.1, 2.0 Hz, Ar$\underline{H}$ para to cyclopentyloxy), 6.80 (1H, d, J 8.1 Hz, Ar$\underline{H}$ ortho to OMe), 7.13 (1H, d, J 5.0 Hz, pyridine $\underline{H}_5$), 8.35 (1H, d, J 5.0 Hz, pyridine $\underline{H}_6$), and 8.71 (1H, br s, pyridine $\underline{H}_2$); m/z 382 (M$^+$, 21%), 315 (19), 314 (89), 313 (39), 178 (12), 137 (100), 43 (32), and 41 (41).

d) 3-(3-Benzylureido)-4-[2-(3-cyclopentyloxy-4-methoxyphenyl)ethyl]pyridine

From the compound of Example 3 a) (399 mg, 1.3 mmol) and benzylisocyanate (0.23 ml, 1.8 mmol) to afford the title compound (477 mg) as a white solid m.p. 152°–154° C. (Found: C, 72.76; H, 7.04; N, 9.36. C$_{27}$H$_{31}$N$_3$O$_3$ requires C, 72.78; H, 7.01; N, 9.43%); $\delta_H$ (CDCl$_3$) 1.5–1.9 (8H, br m, (C$\underline{H}_2$)$_4$), 2.84 (4H, m, C$\underline{H}_2$C$\underline{H}_2$Ar), 3.76 (3H, s, O$\underline{Me}$), 4.36 (2H, d, J 5.7 Hz, NHC$\underline{H}_2$), 4.62 (1H, m, N$\underline{H}$CH$_2$), 4.71 (1H, br m, OC$\underline{H}$), 5.59 (1H, br s, N$\underline{H}$ Ar), 6.52 (1H, d, J 2.1 Hz Ar$\underline{H}$ ortho to cyclopentyloxy), 6.60 (1H, dd, J 8.2, 2.1 Hz, Ar$\underline{H}$ para to cyclopentyloxy), 6.74 (1H, d, J 8.2 Hz, Ar$\underline{H}$ ortho to OMe), 7.10 (1H, d, J 5.0 Hz, pyridine $\underline{H}_5$), 7.2–7.3 (5H, m, C$_6\underline{H}_5$), 8.31 (1H, d, J 5.0 Hz, pyridine H$_6$), and 8.62 (1H, s, pyridine $\underline{H}_2$).

e) N-{4-[2-(3-Cyclopentyloxy-4-methoxyphenyl) ethyl]-3-pyridyl}phenylsulphonamide From the compound of Example 31 (0.416 g, 1.3 mmol) and benzenesulfonylchloride (0.22 ml, 1.6 mmol). Chromatography (SiO$_2$; Et$_2$O) afforded the title comound (0.460 g) as a yellow solid. m.p. 183.9–185.3. Found: C, 66.22; H, 9.76; N, 5.76. C$_{25}$H$_{28}$N$_2$O$_4$S requires C, 63.81; H, 6.42; N, 5.95%). $\delta_H$ (CDCl$_3$) 1.5–1.9 (8H, br m, (C$\underline{H}_2$)$_4$), 2.73 (4H, s, ArC$\underline{H}_2$C$\underline{H}$ pyridine), 3.85 (3H, s, O$\underline{Me}$), 4.62 (1H, br m, OC$\underline{H}$), 5.7 (1H, br s N$\underline{H}$), 6.43 (1H, d, J 2.0 Hz Ar$\underline{H}$ ortho to cyclopentyloxy), 6.59 (1H, dd, J 8.2, 2.0 Hz, ArH para to cyclopentyloxy), 6.82 (1H, d, J 8.2 Hz, Ar$\underline{H}$ ortho to OMe), 7.08 (1H, d, J 4.9 Hz, pyridine $\underline{H}_5$), 7.45–7.5 (2H, m, Ar $\underline{H}$ meta to SO$_2$NH), 7.55–7.6 (1H, m, Ar$\underline{H}$ para to SO$_2$NH), 7.65–7.7 (2H, m, Ar$\underline{H}$ ortho to SO$_2$NH), 8.20 (1H, ca s, pyridine $\underline{H}_2$), and 8.6 (1H, d, J 4.9 Hz, pyridine H$_6$); m/z (EI) 453 (M$^+$+1, 30%), 452 (M$^+$, 98), 385 (24), 384 (100), 383 (16), 243 (14), and 137 (40).

FORMULATION EXAMPLES

The compounds of the invention may be formulated for pharmaceutical use in a number of forms using any suitable excipients. Thus, for example, for oral use the compounds of the invention such as the compounds of the Examples may be formulated as a solid dosage form, by mixing an appropriate weight of compound (for example 50 mg) with maize starch (50–99% w/w), anhydrous colloidal silica (0–10% w/w) and organic or inorganic acid (up to 1% w/w), to fill capsules of an appropriate size, e.g. white opaque hard gelatine capsules size 3. If desired the same mixture may be compressed into tablets.

The activity and selectivity of compounds according to the invention was demonstrated in the following tests. In these tests the abbreviation FMLP represents the peptide N-formyl-met-leu-phe.

Isolated Enzyme

The potency and selectivity of the compounds of the invention was determined using distinct PDE isoenzymes as follows:

i. PDE I, rabbit heart
ii. PDE II, rabbit heart
iii. PDE III, rabbit heart, Jurkat cells
iv. PDE IV, HL60 cells, rabbit brain, rabbit kidney and human recombinant PDE IV
v. PDE V, rabbit lung, guinea pig lung A gene encoding human PDE IV has been cloned from human monocytes (Livi, et al, 1990, *Molecular and Cellular Biology*, 10, 2678). Using similar procedures we have cloned human PDE IV genes from a number of sources including eosinophils, neutrophils, lymphocytes, monocytes, brain and neuronal tissues. These genes have been transfected into yeast using an inducible vector and various recombinant proteins have been expressed which have the biochemical characteristics of PDE IV (*Beavo and Reifsnyder*, 1990, TIPS, 11, 150). These recombinant enzymes, particularly the human eosinophil recombinant PDE IV, have been used as the basis of a screen for potent, selective PDE IV inhibitors.

The enzymes were purified to isoenzyme homogeneity using standard chromatographic techniques.

Phosphodiesterase activity was assayed as follows. The reaction was conducted in 150 µl of standard mixture containing (final concentrations): 50 mM 2-[[tris (hydroxymethyl)methyl]amino]-1-ethane-sulphonic acid (TES) —NaOH buffer (pH 7.5), 10 mM MgCl$_2$, 0.1 µM [$^3$H]-cAMP and vehicle or various concentrations of the test compounds. The reaction was initiated by addition of enzyme and conducted at 30° C. for between 5 to 30 mins. The reaction was terminated by addition of 50 µl 2% trifluoroacetic acid containing [$^{14}$C]-5'AMP for determining recovery of the product. An aliquot of the sample was then applied to a column of neutral alumina and the [$^3$H]-cAMP eluted with 10 ml 0.1 TES-NaOH buffer (pH8). The [$^3$H]-5'-AMP product was eluted with 2 ml 2M NaOH into a scintillation vial containing 10 ml of scintillation cocktail. Recovery of [$^3$H]-5'AMP was determined using the [$^{14}$C]-5'AMP and all assays were conducted in the linear range of the reaction.

Compounds according to the invention such as compounds of the Examples herein cause a concentration-dependent inhibition of recombinant PDE IV at 0.1–1000 nM with little or no activity against PDE I, II, III or V at concentrations up to 100 µM.

2. The Elevation of cAMP in Leukocytes

The effect of compounds of the invention on intracellular cAMP was investigated using human neutrophils or guinea pig eosinophils. Human neutrophils were separated from peripheral blood, incubated with dihydrocytochalasin B and the test compound for 10 min and then stimulated with FMLP. Guinea pig eosinophils were harvested by peritoneal lavage of animals previously treated with intraperitoneal injections of human serum. Eosinophils were separated from the peritoneal exudate and incubated with isoprenaline and test compound. With both cell types, suspensions were centrifuged at the end of the incubation, the cell pellets were resuspended in buffer and boiled for 10 min prior to measurement of cAMP by specific radioimmunoassay (DuPont).

The most potent compounds according to the Examples induced a concentration -dependent elevation of cAMP in neutrophils and/or eosinophils at concentrations of 0.1 nM to 1 µM.

3. Suppression of Leukocyte Function

Compounds of the invention were investigated for their effects on superoxide generation, chemotaxis and adhesion of neutrophils and eosinophils. Isolated leukocytes were incubated with dihydrocyto-chalasin B for superoxide generation only and test compound prior to stimulation with FMLP. The most potent compounds of the Examples caused a concentration-dependent inhibition of superoxide generation, chemotaxis and adhesion at concentrations of 0.1 nM to 1 µM.

Lipopolysaccharide (LPS)-induced synthesis of tumour necrosis factor (TNF) by human peripheral blood monocytes (PBM) is inhibited by compounds of the Examples at concentrations of 0.01 nM to 10 µM.

4. Relaxation of Constricted Airway Smooth Muscle in vitro

The effects of compounds of the invention on guinea-pig isolated tracheal smooth muscle were investigated. Isolated tracheal rings were suspended in organ baths and immersed in oxygenatari Krebs' solution. The smooth muscle was contracted with sub-maximal concentrations of histamine or carbachol prior to the addition of increasing concentrations of test compound to the organ baths. The most potent compounds of the Examples caused a concentration-dependent reversal of both histamine and carbachol-induced contractions at concentrations of 1 nM to 100 µM. The compounds were generally more potent in reversing histamine-induced tone than carbachol-induced tone.

5. Effects on Cardiac Muscle in vitro

Compounds of the invention have been tested for their effects on isolated cardiac muscle. Right atrial and papillary muscles were dissected out from the hearts of guinea pigs and suspended in organ baths for measuring the rate (chronotropic) of spontaneously beating atria and force (inotropic) of the electrically stimulated papillary muscle. In these preparations, selective PDE IV inhibitors such as rolipram do not have any direct effects whereas selective PDE III inhibitors such as milrinone have positive chronotropic and inotropic effects. The non-specific PDE inhibitor theophylline, which is used in asthma as a bronchodilator, also causes significant cardiovascular changes such as tachycardia. Selective PDE IV inhibitors have advantage over theophylline, therefore, through reduced cardiovascular side effects. The most potent and selective compounds of the Examples had no direct effects on the atrial and papillary muscles in vitro at concentrations up to 10 µM but in combination with PDE III inhibitors, these inhibitors showed an enhancement of chronotropic and inotropic activity, typical of selective type IV inhibitors.

6. Anti-inflammatory Activity in vivo

Interleukin-5 (IL-5)-induced pleural eosinophilia in the rat (Lisle, et al, 1993, Br. J. Pharmacol. 108, 230p) is inhibited by compounds of the Examples given orally at doses of 0.0001 to 10.0 mg/kg. The most potent compounds cause a dose-dependent reduction in migrating eosinophils with $ED_{50}$s of 0.003 to 0.03 mg/kg p.o.

Compounds of the invention also reduce the inflammatory responses induced in rats by platelet activating factor (PAF).

7. Anti-allergic Activity in vivo

Compounds of the invention have been tested for effects on an IgE-mediated allergic pulmonary inflammation induced by inhalation of antigan by sensitised guinea pigs. Guinea pigs were initially sensitised to ovalbumin under mild cyclophosphamide-induced immunosuppression, by intraperitoneal injection of antigan in combinations with aluminium hydroxide and pertussis vaccine. Booster doses of antigen were given two and four weeks later and at six weeks, animals were challenged with aerosolised ovalbumin whilst under cover of an intraperitoneally administered anti-histamine agent (mepyramine). After a further 48 h, bronchial alveolar layages (BAL) were performed and the numbers of eosinophils and other leukocytes in the BAL fluids were counted. The lungs were also removed for histological examination for inflammatory damage. Administration of compounds of the Examples (0.001–10 mg/kg i.p. or p.o.), up to three times during the 48 h following antigert challenge, lead to a significant reduction in the eosinophilia and the accumulation of other inflammatory leukocytes. There was also less inflammatory damage in the lungs of animals treated with compounds of the Examples.

8. Effects on Pulmonary Dynamics

Compounds of the invention (0.001–10 mg/kg by oral or other route of aministration) reduce the allergic bronchoconstruction caused by antigen in sensitized guinea pigs.

Compounds of the invention have been tested for their effects on ozone-induced hyperreactivity of the airways of guinea pigs. Following the inhalation of ozone, guinea pigs become very much more sensitive to the bronchoconstrictor effects of inhaled histamine than naive animals (Yeadon et al, 1992, Pulmonary Pharm., 5, 39). There is a pronounced shift to the left (10–30 fold) of the dose response curve to histamine and a highly significant increase in the maximum increase in pulmonary resistance. Compounds of the Examples administered 1 h prior to ozone by the intraperitoneal or oral (0.001–10 mg/kg) route caused a dose-dependent inhibition of ozone-induced hyperreactivity.

9. Adverse Effects

In general, in our tests above, compounds of the invention have had no observed toxic effects when administered to animals at the doses shown.

We claim:

1. A compound of formula (1)

wherein

Y is a halogen atom or a group —$OR^1$, where $R^1$ is an optionally substituted alkyl group;

X is —O—, —S—, or —N(R⁷)—, where R⁷ is a hydrogen atom or an alkyl group;

R² is an optionally substituted cycloalkyl or cycloalkenyl group;

R³ and R⁴, which may be the same or different, is each a hydrogen atom or an alkyl, —CO₂R⁸ (where R⁸ is a hydrogen atom or an optionally substituted alkyl, aryl, or aralkyl group), —CONR⁹R¹⁰ (where R⁹ and R¹⁰ which may be the same or different is each a hydrogen atom or an alkyl, aryl or aralkyl group), —CSNR⁹R¹⁰, —CN, or —CH₂CN group;

Z is —(CH₂)ₙ— where n is zero or an integer 1, 2 or 3;

R⁵ is an optionally substituted 4-pyridyl group;

R⁶ is a hydrogen atom or a hydroxyl group;

and the salts, solvates, hydrates, prodrugs and N-oxides thereof.

2. A compound according to claim 1 wherein Y is a group —OR¹.

3. A compound according to claim 2, where R¹ is an optionally substituted straight or branched C₁₋₃alkyl group.

4. A compound according to claim 3 wherein R¹ is a —CH₃ group.

5. A compound according to any of claim 1 wherein X is —O—.

6. A compound according claim 1 wherein R² is a cyclopentyl group.

7. A compound according to claim 1 wherein Z is a —(CH₂)ₙ— group where n is zero or an integer 1 or 2.

8. A compound according to claim 7 wherein Z is a —(CH₂)ₙ— group where n is zero.

9. A compound according to claim 1 wherein R³ is a hydrogen atom or a —CH₃ group.

10. A compound according to claim 9 where R³ is a hydrogen atom.

11. A compound according to claim 1 wherein R⁴ is a hydrogen atom or an optionally substituted C₁₋₃alkyl or —CN group.

12. A compound according to claim 11 wherein R⁴ is a hydrogen atom or a —CN group.

13. A compound according to claim 1 wherein R⁶ is a hydrogen atom.

14. A compound according to claim 1 wherein the 4-pyridyl group is substituted by one or more substituents R¹¹ wherein R¹¹ is an atom or group R¹² or —Alk¹(R¹²)ₘ wherein R¹² is a halogen atom, or an amino (—NH₂), substituted amino, nitro, cyano, hydroxyl (—OH), substituted hydroxyl, cycloalkoxy, formyl, carboxyl (—CO₂H), esterified carboxyl, thiol (—SH), substituted thiol, —C(O)R⁸ᵃ, (where R⁸ᵃ is a hydrogen atom or an optionally substituted alkyl, aralkyl or aryl group), —SO₃H, —SO₂R⁸ᵃ, —SO₂N(R⁸ᵃ)(R⁹ᵃ), (where R⁹ᵃ is as defined for R⁸ᵃ and may be the same as or different to R⁸ᵃ), —CON(R⁸ᵃ)(R⁹ᵃ), —NHSO₂R⁸ᵃ, —N[SO₂R⁸ᵃ]₂, —NHSO₂N(R⁸ᵃ)(R⁹ᵃ), —NHC(O)R⁸ᵃ, or —NHC(O)OR⁸ᵃ group; Alk¹ is a straight or branched C₁₋₆alkylene, C₂₋₆alkenylene, or C₂₋₆alkynylene chain optionally interrupted by one, two, or three —O—, or —S— atoms or —S(O)p—, or —N(R⁷)— (where R⁷ is a hydrogen atom or an optionally substituted alkyl group) groups; and m is zero or an integer 1,2 or 3.

15. A compound according to claim 14 wherein R¹¹ is a halogen atom or a nitro, amino, alkoxy, haloalkyl, hydroxy, —NHCOR⁸ᵃ, —NHCONHR⁸ᵃ, or —NHSO₂R⁸ᵃ group.

16. A compound which is:

4-[2-(3-Cyclopentyloxy-4-methoxyphenyl)ethyl] pyridine;

(±)-3-(3-Cyclopentyloxy-4-methoxyphenyl)-2-(4-pyridyl)propanenitrile;

3-Benzamido-4-[2-(3-cyclopentyloxy-4-methoxyphenyl) ethyl]pyridine;

N-{4-[2-(3-Cyclopentyloxy-4-methoxyphenyl)ethyl]-3-pyridyl}phenylsulphonamide;

4-[2-(3-Cyclopentyloxy-4-methoxyphenyl)ethyl]-3,5-dichloropyridine;

3-Amino-4-[2-(3-cyclopentyloxy-4-methoxyphenyl) ethyl]pyridine;

4-[2-(3-Cyclopentyloxy-4-methoxyphenyl)ethyl]-3-isobutylamidopyridine; or 3- (3- Benzylureido)-4-[2-(3-cyclopentyloxy-4-methoxyphenyl)ethyl]pyridine;

and the salts, solvates, hydrates and N-oxides thereof.

17. A pharmaceutical composition comprising a compound of formula (1):

wherein

Y is a halogen atom or a group —OR¹, where R¹ is an optionally substituted alkyl group;

X is —O—, —S—, or —N(R⁷)—, where R⁷ is a hydrogen atom or an alkyl group;

R² is an optionally substituted cycloalkyl or cycloalkenyl group;

R³ and R⁴, which may be the same or different, is each a hydrogen atom or an alkyl, —CO₂R⁸ (where R⁸ is a hydrogen atom or an optionally substituted alkyl, aryl, or aralkyl group), —CONR⁹R¹⁰ (where R⁹ and R¹⁰ which may be the same or different is each a hydrogen atom or an alkyl, aryl or aralkyl group), —CSNR⁹R¹⁰, —CN, or —CH₂CN group;

Z is —(CH₂)ₙ— where n is zero or an integer 1, 2 or 3;

R⁵ is an optionally substituted 4-pyridyl;

R⁶ is a hydrogen atom or a hydroxyl group;

and the salts, solvates, hydrates, prodrugs and N-oxides thereof, together with one or more pharmaceutically acceptable carriers, excipients or diluents.

* * * * *

UNITED STATES PATENT AND TRADEMARK OFFICE
CERTIFICATE OF CORRECTION

PATENT NO. : 5,739,144
DATED : April 14, 1998
INVENTOR(S) : Warrellow et al.

It is certified that error appears in the above-identified patent and that said Letters Patent is hereby corrected as shown below:

Column 5,
Line 66, delete "morpheline" and insert -- morpholine -- therefor;

Column 10,
Line 16, delete "R6" and insert -- $R^6$ -- therefor;

Column 12,
Line 14, delete "AIK" and insert -- A1K -- therefor;
Line 23, delete "arthydride" and insert -- anhydride -- therefor;
Line 64, delete "1 00" and insert -- 100 -- therefor;

Column 15,
Line 27, delete "orthoto" and insert -- ortho to -- therefor;
Line 45, delete "PY$\underline{H}_2$" and insert -- Py$\underline{H}_2$ -- therefor;
Line 48, delete "312" and insert -- 3[2 -- therefor;

Column 16,
Line 41, delete "Cyclopentylpxy" and insert -- Cyclopentyloxy -- therefor;

Column 18,
Line 31, delete "(1 500" and insert -- (1500 -- therefor;
Line 56, delete "cyclppentyloxy" and insert -- cyclopentyloxy -- therefor;
Line 61, delete "recrystaliised" and insert -- recrystallised -- therefor;

Column 21,
Line 62, delete "C$\underline{H}$" and insert -- C$\underline{H}_2$, -- therefor;

Column 22,
Line 59, delete "trifiuoroacetic" and insert -- trifluoroacetic -- therefor;

Column 24,
Line 27, delete "layages" and insert -- lavages -- therefor;
Line 33, delete "antigert" and insert -- antigen -- therefor;
Line 39, delete "aministration" and insert -- administration -- therefor;

UNITED STATES PATENT AND TRADEMARK OFFICE
CERTIFICATE OF CORRECTION

PATENT NO.   : 5,739,144
DATED        : April 14, 1998
INVENTOR(S)  : Warrellow et al.

It is certified that error appears in the above-identified patent and that said Letters Patent is hereby corrected as shown below:

Column 25,
Line 15, delete "solyates," and insert -- solvates -- therefor;
Line 48, after "formyl" insert -- [HC(O)-] -- therefor;

Column 26,
Line 51, after "4-pyridyl" insert -- group -- therefor;

Signed and Sealed this

Twenty-fifth Day of March, 2003

JAMES E. ROGAN
*Director of the United States Patent and Trademark Office*